(12) United States Patent
Ford et al.

(10) Patent No.: US 6,269,340 B1
(45) Date of Patent: *Jul. 31, 2001

(54) INFUSION PUMP WITH AN ELECTRONICALLY LOADABLE DRUG LIBRARY AND A USER INTERFACE FOR LOADING THE LIBRARY

(75) Inventors: Alan D. Ford, Concord, NH (US); Nathaniel M. Sims, Wellesley Hills, MA (US); Marc A. Mandro, Bow, NH (US)

(73) Assignees: The General Hospital, Boston, MA (US); Baxter International, Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/957,907

(22) Filed: Oct. 27, 1997

Related U.S. Application Data

(62) Division of application No. 08/665,828, filed on Jun. 19, 1996, now Pat. No. 5,681,285, which is a continuation of application No. 07/961,527, filed on Oct. 15, 1992.

(51) Int. Cl.[7] .................................................. A61M 5/14
(52) U.S. Cl. .......................... 705/3; 604/890.1; 604/19; 604/67
(58) Field of Search ..................... 604/890.1, 19, 604/151, 31, 65, 66, 67, 155; 705/3, 2

(56) References Cited

U.S. PATENT DOCUMENTS

| | | | |
|---|---|---|---|
| 3,809,871 | * | 5/1974 | Howard et al. ...................... 604/131 |
| 4,464,172 | * | 8/1984 | Lichtenstein ........................... 604/65 |
| 4,502,488 | * | 3/1985 | Degironimo et al. ............... 604/246 |
| 4,544,369 | * | 10/1985 | Skakoon et al. ..................... 604/155 |
| 4,696,671 | * | 9/1987 | Epstein et al. ......................... 604/67 |
| 4,741,732 | * | 5/1988 | Crankshaw et al. .................. 604/67 |
| 4,756,706 | * | 7/1988 | Kerns et al. ............................ 604/66 |

(List continued on next page.)

FOREIGN PATENT DOCUMENTS

| | | | | |
|---|---|---|---|---|
| 0 364 010 | * | 4/1990 | (EP) | ................................ A61M 5/14 |
| 0 497 041 A1 | * | 8/1992 | (EP) | ............................... A61M 5/172 |
| WO 88/10383 | * | 12/1988 | (WO) | .............................. A61M 5/20 |

OTHER PUBLICATIONS

Bazaral et al, "Recommendations for Specifications and Operator Interface Design for New Medical Infusion Pumps", Biomedical Instrumentation & Technology, 2:364–370, Sep.–Oct. 1992.*

Crankshaw et al, "How Should We Administer Intravenous Anaesthetic Drugs?", I.V. Anesthesia: What is New?, vol. 5, No. 2, Chapter 4, Sep. 1991.*

Siemens Minimed Infusion System Product Literature, apr. 1992.*

Harvard Apparatus, Syringe and Peristaltic Pumps, 1991, pp. 14–33.*

Bard PCA II Product Literature, Oct. 14, 1992.*

(List continued on next page.)

*Primary Examiner*—James P. Trammell
*Assistant Examiner*—John W. Hayes
(74) *Attorney, Agent, or Firm*—Fish & Richardson P.C.

(57) ABSTRACT

A system for creating a customized drug library for an electronically loadable drug infusion pump, the system including a drug library containing a plurality of drug entries, there being associated with each drug entry a set of associated drug delivery parameters and/or drug delivery protocols for configuring the drug infusion pump; a tool for selecting a set of drug entries from among the plurality of drug entries in said drug library; a tool for adding the selected drug entries along with the sets of drug delivery information associated therewith to a customized library; and a loading tool for causing the system to electronically load the customized library into the drug infusion pump.

32 Claims, 18 Drawing Sheets

U.S. PATENT DOCUMENTS

| | | | |
|---|---|---|---|
| 4,853,521 | * | 8/1989 | Claeys et al. .................... 604/407 |
| 4,898,578 | * | 2/1990 | Rubalcaba, Jr. .................. 604/66 |
| 4,925,444 | * | 5/1990 | Orkin et al. ...................... 604/65 |
| 4,942,883 | * | 7/1990 | Newman ........................... 604/20 |
| 4,943,279 | * | 7/1990 | Samiotes et al. ................. 604/67 |
| 4,978,335 | * | 12/1990 | Arthur, III ........................ 604/67 |
| 5,034,004 | * | 7/1991 | Crankshaw ....................... 604/67 |
| 5,078,683 | * | 1/1992 | Sancoff et al. ................... 604/67 |
| 5,088,981 | * | 2/1992 | Howson et al. .................. 604/67 |
| 5,153,827 | * | 10/1992 | Coutre et al. .................... 604/66 |
| 5,256,157 | * | 10/1993 | Samiotes et al. ................. 604/67 |
| 5,317,506 | * | 5/1994 | Coutre et al. .................... 604/65 |
| 5,772,635 | * | 6/1998 | Dastur et al. .................... 604/67 |

OTHER PUBLICATIONS

Siemens MiniMed III Infusion System–Life Support Systems Product Literature, Oct. 14, 1992.*

Omni–Flow 4000 Operations Manual, Oct. 14, 1992.*

Glass et al, "Intravenous Anesthetic Delivery", Anesthesia, vol. 1, 1990, pp. 367–388.*

Glass et al, "Intravenous Drug Delivery Systems", Anesthesiology, Raven Press, 1991, pp. 23 and 34.*

Jacobs et al, "Technology for Continuous Infusion in Anesthisia", Tntern. Anesth. Clinics, 1991.29(4) publication date, Jan. 1992, pp. 39–49.*

CaiVAS Brochure, Oct. 14, 1992.*

S.H. Juhl et al, "Patient–Controlled Analgesia: A Technical Toy or a Contribution to the Treatment of Pain?", Anaesthesist, 1988 Aug:37(8): 543–550 (Abstract).*

G. Juhl, "The Infucommand: A PCA (Patient–Controlled Analgesia) Device Using Pulsoximetric Bolus Control", anaesthesist, Apr. 1990:39(4):236–239 (Abstract).*

H. Suttmann et al, "Computer–Controlled Inufsion", Anaesthesist, Aug. 1988:37(8):58–561.*

* cited by examiner

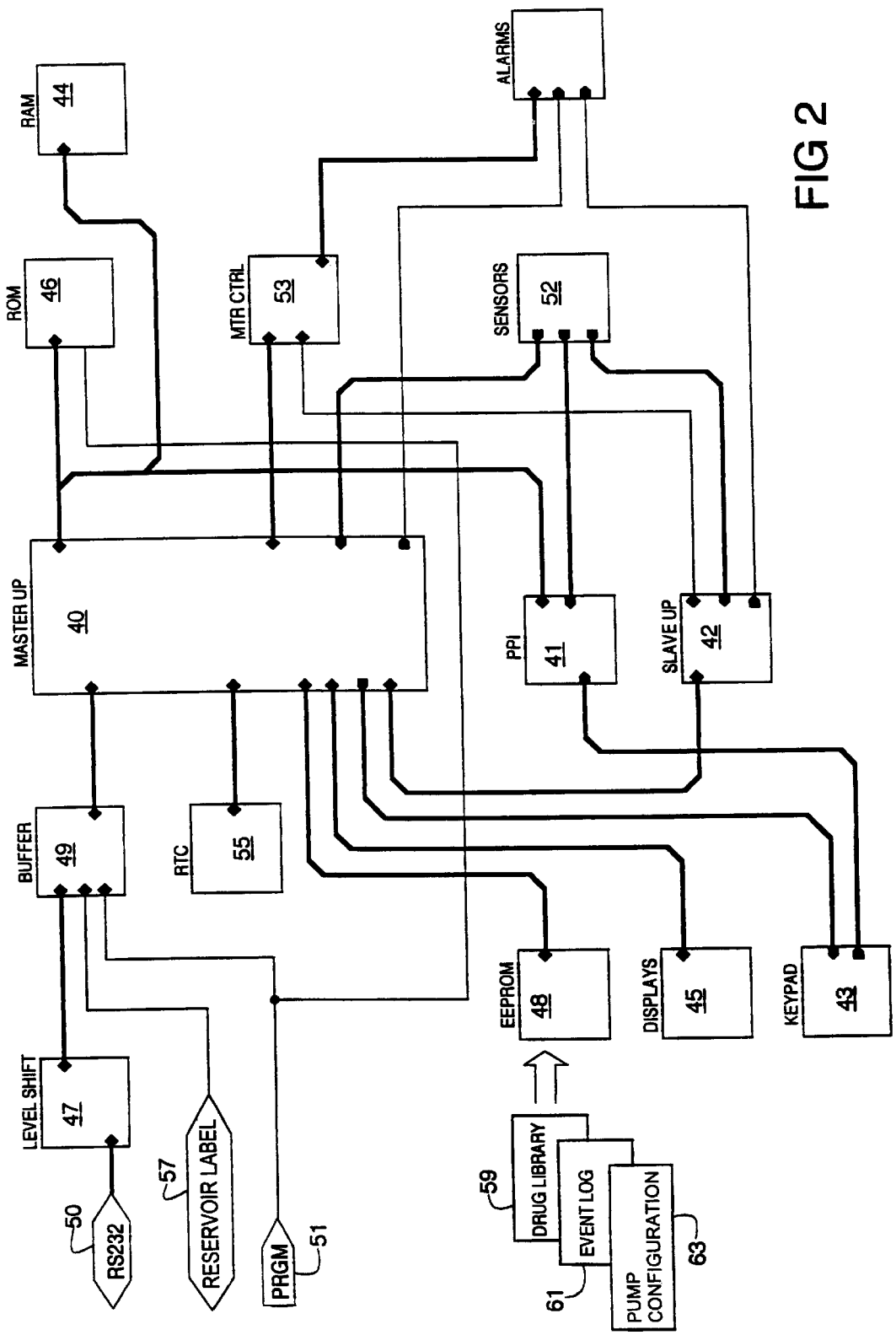

CREATE / EDIT A CUSTOM DRUG

| DRUG NAME & CONCENTRATION | TYPE | min def max — DOSE | min def max — BOLUS | MAX. BOLUS RATE & CONFIG. ON IN PUMP |
|---|---|---|---|---|
| * _ _ _ _ _ mg / m | C | _ _ _ _ _ mcg / kg / min _ _ _ _ _ _ _ _ _ _ | _ _ _ _ _ mcg / kg _ _ _ _ _ _ _ _ _ _ | _ _ _ _ _ mcg / kg / min Config: Y |

F1 = Help
F5 = Toggle drug mode
F6 = Toggle pediatric / adult
ESC = Cancel changes
F9 = Graphical tool
 * = Indicates drug selected TAB = Next field LEFT ARROW = Previous character
RIGHT ARROW = Next Character
DEL = Delete character ENTER = Save and return to drug list

FIG 9

CREATE / EDIT A CUSTOM DRUG

| DRUG NAME & CONCENTRATION | TYPE | min def max — DOSE | min def max — BOLUS | MAX. BOLUS RATE & CONFIG. ON IN PUMP |
|---|---|---|---|---|
| * NEW DRUG 25 mg / ml | C | 100 mcg / kg / min 200 300 | 1 mcg / kg 2 3 | 400 mcg / kg / min Config: Y |

F1 = Help
F5 = Toggle drug mode
F6 = Toggle pediatric / adult
ESC = Cancel changes
 * = Indicates drug selected TAB = Next field LEFT ARROW = Previous character
RIGHT ARROW = Next Character
DEL = Delete character ENTER = Save and return to drug list

FIG 10

| SYRINGES MENU | | | | | | | | |
|---|---|---|---|---|---|---|---|---|
| B-D | 1 ML | Y | MONOJECT | 1 ML | Y | TERUMO | 1 ML | Y |
| B-D | 3 ML | Y | MONOJECT | 3 ML | Y | TERUMO | 3 ML | Y |
| B-D | 5 ML | Y | MONOJECT | 6 ML | Y | TERUMO | 5 ML | Y |
| B-D | 10 ML | Y | MONOJECT | 12 ML | Y | TERUMO | 10 ML | Y |
| B-D | 20 ML | Y | MONOJECT | 20 ML | Y | TERUMO | 20 ML | Y |
| B-D | 30 ML | Y | MONOJECT | 35 ML | Y | TERUMO | 30 ML | Y |
| B-D | 60 ML | Y | MONOJECT | 60 ML | Y | TERUMO | 60 ML | Y |

△ = Previous syr
▽ = Next syr (SPACEBAR) = Change configuration
ENTER = Save and return to main menu

FIG 15

| DEFAULTS MENU | |
|---|---|
| DRUG DEFAULT | Y |
| MODE DEFAULT | Y |
| MFR DEFAULT | Y |
| SYRINGE DEFAULT | Y |

△ = Previous default
▽ = Next default (SPACEBAR) = Change configuration
ENTER = Save and return to main menu

FIG 16

| MISCELLANEOUS FEATURES MENU | |
|---|---|
| DRUG LIBRARY ENABLE | Y |
| SYRINGE RECOGNITION | Y |
| SYRINGE DETECTION | Y |
| PSI RANGE | M |
| RATE RANGE | H |
| AUTO LOCK | N |
| VOLUME LIMIT | Y |
| SILENT RUNNING | N |
| IDLE ALARM | N |

▽ = Previous feature
△ = Next feature
(SPACEBAR) = Change configuration
ENTER = Save and return to main menu

FIG 17

CREATE / EDIT PUMP IDENTIFIER

Type in identifier and press ENTER
(Legal char's: A-Z, 0-9, dash & space)

ESC = Cancel changes
DEL = Delete character
LEFT ARROW = Previous character
RIGHT ARROW = Next character

FIG 18

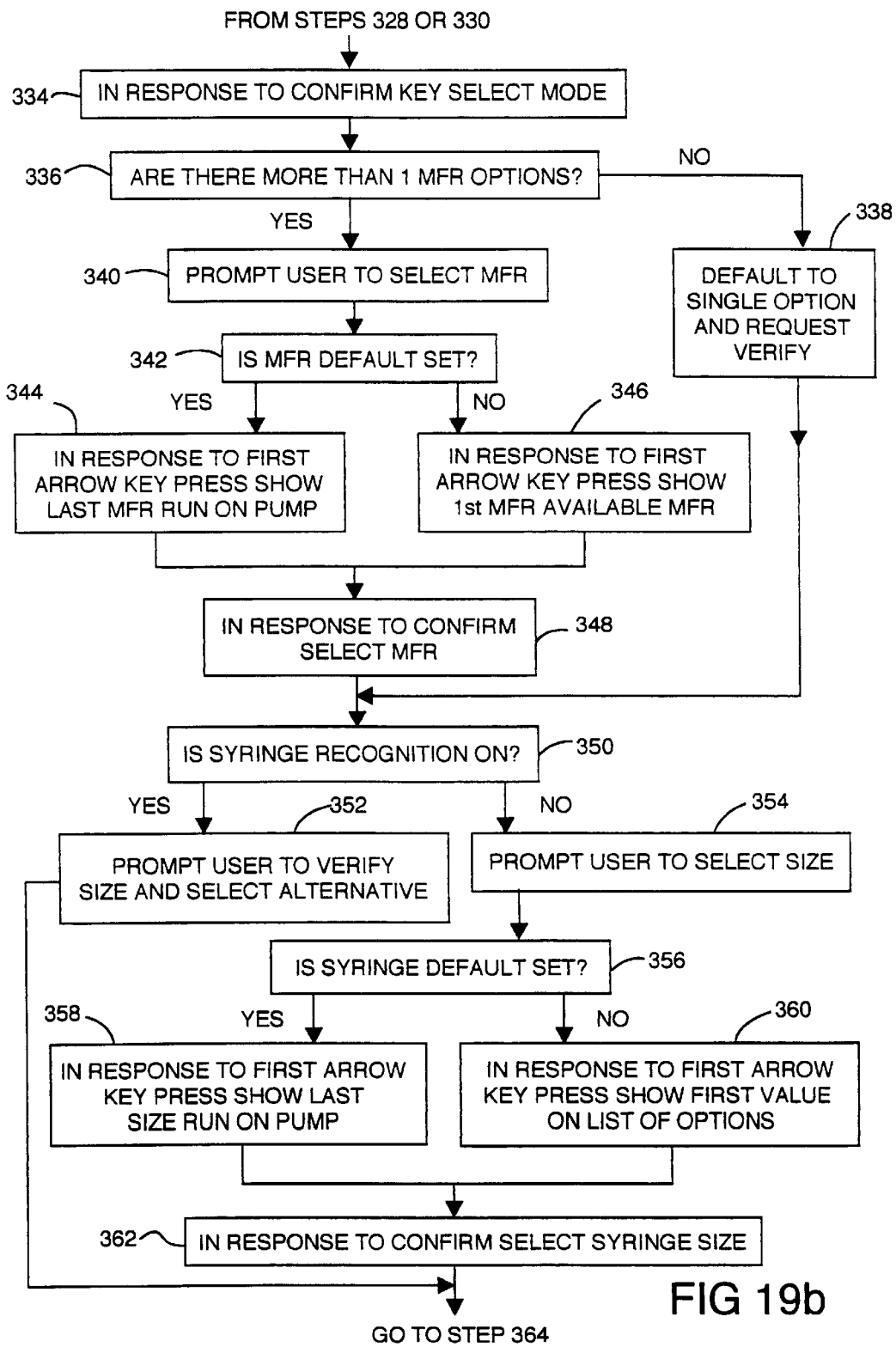

|  | mL / hr | Units / hr | mcg / min | mcg / kg / min |
|---|---|---|---|---|
| 200 | SELECT MODE, SYRINGE MFR, SYRINGE SIZE | SELECT MODE, SYRINGE MFR, SYRINGE SIZE | SELECT MODE, SYRINGE MFR, SYRINGE SIZE | SELECT MODE, SYRINGE MFR, SYRINGE SIZE |
| 202 |  |  |  | ENTER THE PATIENT'S BODY WEIGHT IN KILOGRAMS (kg) |
| 204 |  | ENTER THE DRUG CONCENTRATION IN UNITS PER MILLILITER (U / mL) | ENTER THE DRUG CONCENTRATION IN MILLIGRAMS PER MILLILITER (mg / mL) | ENTER THE DRUG CONCENTRATION IN MILLIGRAMS PER MILLILITER (mg / mL) |
| 206 | ENTER THE INFUSION RATE IN MILLILITERS per hour (mL / hr) | ENTER THE INFUSION DOSE IN UNITS PER HOUR (U / hr) | ENTER THE DOSE IN MICROGRAMS PER MINUTE (mcg / min) | ENTER THE DOSE IN MICROGRAMS PER KILOGRAM PER MINUTE (mcg / kg / min) |
| 208 | ENTER THE VOLUME LIMIT (mL) |  |  |  |
| 210 | ENTER THE BOLUS SIZE IN MILLILITERS (mL) | ENTER THE BOLUS SIZE IN UNITS | ENTER THE BOLUS SIZE IN MILLIGRAMS (mg) | ENTER THE BOLUS SIZE IN MICROGRAMS PER KILOGRAM OF BODY WEIGHT (mcg / kg) |
| 212 | PURGE system | PURGE system | PURGE system | PURGE system |
| 214 | Press < START > | Press < START > | Press < START > | Press < START > |

FIG 24

INFUSION PUMP WITH AN ELECTRONICALLY LOADABLE DRUG LIBRARY AND A USER INTERFACE FOR LOADING THE LIBRARY

This is a divisional of application Ser. No. 08/665,828, filed Jun. 19, 1996, now issued as U.S. Pat. No. 5,681,285, which is, in turn, a continuation of application Ser. No. 07/961,527, filed Oct. 15, 1992.

BACKGROUND OF THE INVENTION

The invention relates to programmable drug infusion pumps.

Infusion pumps as used in the field of health care are electromechanical devices which control the flow rate of medical fluids. An example of a drug infusion pump is the AS40A® Infusion Pump by Baxter Healthcare Inc. It operates a medical syringe to deliver a drug to a patient at a precisely controlled rate. The AS40A employs an active fluid pumping mechanism, i.e., positive displacement of the syringe plunger, to expel fluid from the syringe. This type of pump is generally known as a syringe pump.

A vital application for infusion pumps in the human and veterinary medical field is in the delivery of chemicals, drugs, nutrition, or biological products to patients. Typically, in these applications, one or more drugs or other substances are mixed into a uniform solution in a medical fluid and are then delivered through an infusion pump into the bloodstream of a recipient via tubing and/or catheters which conduct the fluid from the pump to the recipient's vascular space.

The fluid flow rate or sequence of rates at which an infusion pump operates are typically selected based on a desired pattern of drug delivery appropriate to the specific circumstance. There are numerous factors that should be considered in the process of specifying a specific rate of fluid flow from a pump at a particular moment in time. Those factors may include:

(i) the nature of the substance being infused, including the known pharmacokinetics and pharmacodynamics of a drug;
(ii) the concentration or dilution of the substance in the fluid;
(iii) the recipient, including sex, age, various measures of weight or size, the state of function of various organ systems, and ability to tolerate infusion of various diluent fluid volumes;
(iv) the occurrence of change in measurable endpoints related to the actions or effects of the substance being infused;
(v) the difference between the estimated concentration of the drug at the target site of drug action (as computed based upon actual measurements or based upon pharmacokinetic models and the prior history of the infusion and/or other factors), as compared to the desired concentration;
(vi) local practices, policies, protocols, and regulations; or
(vii) other considerations including operator judgement.

The process by which a patient care-giver takes the above considerations into account and chooses fluid flow rates for drug delivery from a pump is complex and if done incorrectly can lead to serious problems. The process is prone to error, especially because of the requirement for multiple computations and calculations. The complexities are aggravated by several factors. The staff training cost and the cost of preparing, updating, and distributing formularies and policy and procedure protocols within hospitals is large. The difficulty of establishing safe and uniform practices is compounded by significant local, regional, and nation-to-nation variations in practice patterns. The complexity of using such pumps may result in denial of needed therapy to patients because a care-giver lacks sufficient training, or does not have ready access or the time to review relevant knowledge or to use other tools (such as computational devices) to effect the process of delivering a needed medication infusion to a specific patient.

Various technological approaches have been taken in the past to make infusion pumps more suitable for intravenous drug infusions. For example, companies have developed calculator-type infusion pumps which allow users to deliver drug diluted in a fluid by entering data such as drug concentration, patient weight, and desired doses and dose rates using dose delivery units such as mcg/kg or mcg/kg/min. Based upon these inputs, the pumps calculate the volumes and fluid flow rates to be delivered.

Some pumps include physical templates which can be attached to and which electromagnetically modify (i.e., program) the infusion pump. These templates are drug-, drug-concentration-, drug-container-size-, bolus-rate-, and dose-delivery-unit-specific. The templates contain knowledge which is useful for end-users in that typical drug delivery doses and dose rates are printed on the physical templates. For each drug delivery configuration there must be a separate template. In addition, if a particular drug delivery configuration will be used simultaneously on multiple pumps within a facility, there must be available an equal number of identical templates, one for each pump.

Other approaches to making fluid infusion pumps more suitable for drug infusion have included the development of pumps which contain digital communication ports for external control. These permit the infusion pump to be continuously cabled to a separate remote personal computing device. The personal computer can then run a particular program tailored to provide the desired pattern of drug delivery appropriate to the specific circumstance.

Still other approaches to making fluid infusion pumps more suitable for drug infusion have included the development of pumps which contain microprocessor controllers and EPROM devices containing preprogrammed information including a series of drug infusion profiles relating to various drugs to be infused (See PCT International Publication No. WO 88/10383 entitled "Infusion Pump and Drive Systems Therefore"). A related approach, which is described by Crankshaw et al. in U.S. Pat. No. 4,741,732, involves use of EPROM modules which can be physically plugged into the pump casing. The modules are drug-specific and thus a separate module is required for each drug type. The program within a module varies the infusion rate over time according to a predefined drug delivery profile algorithm.

SUMMARY OF THE INVENTION

Applicants have recognized both the limitations of prior drug infusion technologies and the consequent risk to patients, and have developed a customizable drug library software capability for infusion pumps which avoids those limitations and consequent risks. The electronically customizable drug library, either by itself or interacting with an automatic drug recognition capability based upon a machine readable label or data carrier, avoids problems of the prior approaches and both facilitates and enhances the dissemination, training, and execution of appropriate and customary drug infusion practices found in critical care areas of hospitals.

In general, in one aspect, the invention is a system for creating a customized drug library for an electronically loadable drug infusion pump. The system includes a drug library containing a plurality of drug entries, there being associated with each drug entry a set of associated drug delivery parameters and/or drug delivery protocols for configuring the drug infusion pump. It includes means for selecting a set of drug entries from among the entries in said drug library; means for adding the selected drug entries along with the sets of drug delivery information associated therewith to a customized library; and loading means for causing the system to electronically load the customized library into the drug infusion pump.

Preferred embodiments include the following features. Each of the associated sets of drug delivery parameters includes information selected from a group of parameters including drug concentration, drug delivery rate, drug dose, and bolus size. The group of parameters includes minimum, default and maximum drug delivery rate; minimum, default and maximum dose; minimum, default and maximum bolus size; and maximum bolus rate. The system also includes means for creating a drug configuration within the customized library that does not exist in the drug library. The system further includes means for editing an existing drug configuration in the customized library. In addition, the system includes a graphical tool that generates a graph for display on a computer screen, the graph enabling the user to select an appropriate drug concentration for a given body weight. The graph is a two-dimensional log—log graph wherein one axis is body weight and the other axis is fluid flow rate. There are one or more curves plotted on the graph, each of the one or more curves being for a given drug concentration and different doses. The one or more curves are of the form:

$$\text{Body Weight} = \text{Rate} \times \frac{\text{Concentration}}{\text{Dose}} \times K,$$

where K is a positive number. The system further includes means for moving the one or more curves about on the graph.

Preferred embodiments also include the following features. The system includes a list of available mode options, means for identifying one or more modes from that list and means for adding the identified modes to the customized library. The modes specify the units available for expressing the drug delivery information and the identified modes are those the modes that will be available in the infusion pump when the customized library is loaded into the infusion pump. The available mode options include milliliter/hour, units/hour, micrograms/minute, and micrograms/kilogram/minute. The system also includes a list of names of syringe manufacturers, means for selecting names of syringe manufacturers from that list and means for adding the selected names of syringe manufactures to the customized library. The selected names of syringe manufacturers identify syringes that can be used in the drug infusion pump when the customized library is loaded into the infusion pump. The system further includes a list of syringe sizes, means for one or more syringe sizes from that list and means for adding the selected syringe sizes to the customized library.

Also in preferred embodiments, the system includes means for representing a set of features within the customized library, each of which can be toggled on or off, and means for toggling on or off each of the features. The set of features includes a drug library enable flag, wherein the drug library enable flag either enables or disables, depending upon the condition of the drug library enable flag, access to the drug entries within the customized library when the customized library is loaded into said drug infusion pump. The set of features includes a syringe recognition flag, wherein the syringe recognition flag either enables or disables, depending upon the condition of the syringe recognition flag, a syringe recognition capability within the drug infusion pump when the customized library is loaded into the drug infusion pump. The set of features includes a syringe detection flag, wherein the syringe detection flag either enables or disables, depending upon the condition of the syringe detection flag, a syringe detection capability within the drug infusion pump when the customized library is loaded into the drug infusion pump. The set of features includes a volume limit detection flag, wherein the volume limit flag either enables or disables, depending upon the condition of the volume limit flag, a function within the pump that enables the user to specify a volume limit for a drug delivery configuration when the customized library is loaded into the drug infusion pump.

In addition, preferred embodiments include means for causing the system to read pump configuration information from the drug infusion pump. In the system, the means for selecting is normally disabled and the system further includes password protection logic that serves to enable the selection means but only if a system user supplies a preselected password to the password protection logic. There are a plurality of access levels, each of which corresponds to a different set of access privileges in the system and the system includes a table associating each of a plurality of users with a corresponding one of the access levels and the password protection logic uses that table to assign access privileges to the system user. The system also includes an access control means for controlling access to the loading means, wherein the access control means permits access to the loading means if a system user satisfies a set of preconditions and denies access to the loading means if the system user fails to satisfy the set of preconditions. The access control means includes a sign-off table for recording a sign-off and the access control means permits access to the loading means if a valid approval sign-off exists in the sign-off table and denies access to the loading means if a valid approval sign-off does not exist in the sign-off table. The sign-off table includes an system user name and a system user date and time and an approval name and an approval date and time. The system user date and time records when a last modification of the customized file by the user occurred and the access control means permits access to the loading means if the approval date and time is later than the system user date and time and denies access to the loading means if the approval date and time is later than the system user date and time.

In general, in another aspect, the invention is a system for use with a computer. The system includes a storage medium containing a drug library, the drug library containing a plurality of drug entries, there being associated with each drug entry a set of associated drug delivery information for configuring a programmable drug infusion pump, the storage medium being readable by the computer. The system also includes a program that runs on the computer, the program including means for enabling a user to select a set of drug entries from among the plurality of drugs entries in the drug library; means for enabling the user to add the selected drug entries along with the sets of drug delivery information associated therewith to a customized library; and means for enabling the user to cause the computer to electronically load the customized library into the drug infusion pump.

In general, in yet another aspect, the invention is a drug infusion pump for use with a container containing a particular drug. The pump includes a drive mechanism for causing the particular drug to be delivered to a patient from the container; a programmable controller controlling the drive mechanism; an electronically loadable memory inside the pump; input circuitry through which the electronically loadable memory can be electronically loaded with a drug library, the drug library containing a plurality of drug entries, there being associated with each drug entry a set of associated drug delivery parameters and/or drug delivery protocols for configuring the drug infusion pump; a user interface enabling a user to program the programmable controller. The user interface includes means for enabling the user to select a drug entry from the electronically loaded drug library; and means for configuring the programmable controller with the set of drug delivery parameters associated with the selected drug.

Preferred embodiments include the following features. The container is a syringe and the drive mechanism operates the syringe. The electronically loadable memory is non-volatile memory, e.g. EEPROM. The user interface includes a control panel through which the user can program the programmable controller and a display screen for displaying drug entries from the drug library. Each of the associated sets of drug delivery parameters includes information selected from a group of parameters including drug concentration, drug delivery rate, drug dose, and bolus size. The electronically loaded drug library contains a list of available mode options specifying the units available for expressing drug delivery information, and the drug infusion pump offers the user the list of available mode options from which to make a selection when the electronically loaded drug library is in the pump. The electronically loaded drug library contains a list of names of syringe manufacturers identifying syringes that can be used in the drug infusion pump, and the drug infusion pump offers the user the list of names of syringe manufacturers from which to make a selection when the electronically loaded drug library is in the pump. The loaded drug library contains a list of syringe sizes identifying syringes that can be used in the drug infusion pump, and the drug infusion pump offers the user the list of syringe sizes from which to make a selection when the electronically loaded drug library is in said pump. The loaded drug library contains a set of features, each of which is either be toggled on or off, and the pump offers the user only the features from among the set of features that are toggled on when the electronically loaded drug library is in said pump.

In general, in still another aspect, the invention is a drug infusion pump for use with a container containing a given drug, the container including a machine readable label, the label specifying an identifier of the given drug and possibly other information about the given drug. The pump includes a drive mechanism for causing the given drug to be delivered to a patient from the container; a programmable controller controlling the drive mechanism; a memory for storing a drug library containing a plurality of drug entries, there being associated with each drug entry a set of associated drug delivery parameters for configuring the drug infusion pump; a label reader for reading the contents of the label on the container; means responsive to the label reader for identifying an entry in the drug library that corresponds to the given drug; means for configuring the programmable controller by using the set of drug delivery parameters associated with the identified entry from the drug library; and means for causing the controller to run the drive mechanism using the set of drug delivery parameters associated with the identified entry from the drug library.

In preferred embodiments, the machine readable label is a touch memory. In addition, the label includes an expiration date for the given drug and the pump includes an internal clock indicating a current date; means for comparing the expiration date as read by the label reader to the current date as indicated by the internal clock; and means for issuing a warning if the current date is later than the expiration date. The pump further includes means for preventing the controller from running the drive mechanism if the current date is later than the expiration date.

In general, in another aspect, the invention is a drug infusion pump including a drive mechanism for causing the given drug to be delivered to a patient from the container; a programmable controller controlling the drive mechanism; a memory containing an event log; means for configuring the programmable controller to deliver the given drug in accordance with a set of drug delivery parameters; a user interface for operating the pump; and means for creating in the event log a sequence of event records, each event record documenting a different event in the operation and/or programming of the pump.

In preferred embodiments, the events that are recorded in the event log include occurrences of alarms.

A significant advantage of the present invention is that it enables clinicians to easily customize their drug infusion pumps by electronically injecting customized drug libraries and configuration data into them. Thus, the clinicians can easily customize their drug infusion pumps with drug-associated information that the clinician has heretofore had to remember.

The invention offers users ease in customizing their pumps to reflect exactly the unique clinical practices and preferences of a community of users (typically a single hospital, or a subset of users within that hospital) sharing a group of infusion pumps, thus essentially incorporating the written practices, policies, and procedures within the device, at the point of use.

The electronic customizability of drug infusion pumps allows hospital-based users continually and easily to update their infusion devices to reflect new drug introductions, modifications or minor variants of dosing regimens, local practices with respect to the compounding together of several medications in one fluid container, and advances in medical knowledge.

The interaction between the internal drug library and the automated drug recognition capability using machine readable labels provides a seamless link between drug container-associated information and pump resident information or knowledge necessary for infusions.

The ability to log pump events and to download them from the pump to a personal computer enables clinicians to perform automated record-keeping relative to drug infusion history for a specific patient, and to collect device utilization information.

The invention offers users the ability (using the graphical tool) to perform "what-if" prospective analysis of the impact of a particular choice of drug concentration or mixing upon the fluid flow rates which would result if certain doses or dose rates were chosen for patients of various body sizes.

The invention provides the users with a layer of safety in terms of preventing programming errors during the set-up of an infusion pump as, for example, entering 0.02 instead of 0.2.

Other advantages and features will become apparent from the following description of the preferred embodiments and from the claims.

BRIEF DESCRIPTION OF THE DRAWINGS

FIG. 2 is a block diagram of the circuitry within the infusion pump of FIG. 1;

FIG. 9 shows an empty Create/Edit A Custom Drug screen that is accessible by pressing F3/F2 when viewing the Drug List screen;

FIG. 10 shows a Create/Edit A Custom Drug screen that contains information for "New Drug", a user created drug;

FIG. 15 shows a Syringes Menu screen that is accessible by selecting the "CONFIGURE SYRINGES" option in the Main Menu;

FIG. 16 shows a Defaults Menu screen that is accessible by selecting the "CONFIGURE DEFAULTS" option in the Main Menu;

FIG. 17 shows a Miscellaneous Features Menu that is accessible by selecting the "CONFIGURE MISC" option in the Main Menu;

FIG. 18 shows a Create/Edit Pump Identifier screen that is accessible by selecting the "CONFIGURE IDENT" option in the Main Menu;

FIGS. 19a–c is a flow chart of the program within the pump that enables the user to configure the pump to run a particular drug delivery schedule.

FIG. 24 is a table showing the procedures for programming the pump when the drug library is not enabled.

DESCRIPTION OF THE PREFERRED EMBODIMENT(S)

The Drug Infusion Pump

Figure 1:
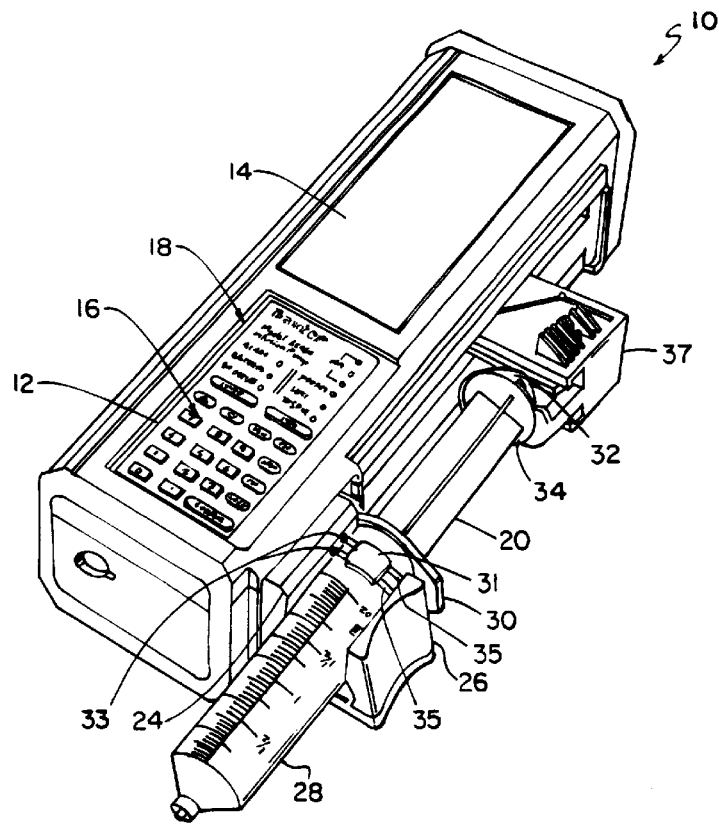
FIG. 1 shows a drug infusion pump that incorporates an electronically loadable drug library.

Referring to FIG. 1, a portable infusion pump 10 with an internal memory for storing an electronically loadable drug library includes a user interface consisting of a control panel 12 and a data display 14. Control panel 12 includes a keyboard 16 and a group of status lights 18. Keyboard 16 is a conventional vented-membrane type, using a tactile feedback silicone rubber overlay. Data display 14 is an LCD screen on which drug infusion information can be displayed. Status lights 18 are an array of LEDs that are used to display pump status information. There is also a single audio transducer (not shown).

On the right side of the infusion pump, there is a pair of clamping devices for holding a syringe 20 that has a barrel 28, a flange 30 and a plunger 34. One of the clamping devices is a barrel clamp affixed to the body of pump 10. It includes a barrel clamp cradle 24 and a barrel clamp slider 26 that can be pressed against barrel 28 to grasp syringe 20 and hold it in a fixed position. The barrel clamp operates by simultaneously capturing both barrel 28 and flange 30 of syringe 20. Also on the same side of pump 10 as the barrel clamp is a plunger driver 37 with a plunger clamp 32. It is connected to the internal drive mechanism (not shown). Plunger clamp 32 grasps plunger of the syringe and, when pump 10 is running, plunger driver 37 pushes plunger 34 into syringe barrel 28 at a controlled speed to achieve the desired drug delivery rate. Plunger clamp 32 and the plunger drive mechanism effectively control movement of the plunger in the axial direction, thus limiting the potential for unintended drug flow due to siphoning. The internal drive mechanism uses a lead screw/split-nut drive and is designed so that the drive is disengaged when plunger clamp 32 is in the "open" position thereby allowing the syringe to be removed and plunger driver 37 to be moved manually to any desired starting position.

Mounted on syringe 20 is a touch memory chip 31 such as is available from Dallas Semiconductor. This chip stores information about the syringe including the date on which its contents were prepared, the identity of the person who prepared the drug, the name of the drug, its concentration, the syringe manufacturer and size, and possibly other drug related information, such as pharmacokinetic model-based drug infusion schedules and drug delivery profiles. Pump 10 includes a two contacts 33 which are used to read the contents of touch memory chip 31 into internal memory. Touch memory chip 31 (also referred to as a machine readable label) is in electrical contact with two conductor strips 35, each of which is contacted by a different one of the two contacts 33 when the syringe is mounted in the pump. The electrical contact with conductor strips 35 enables the touch memory to transfer its contents into internal memory in the pump.

The motor which drives plunger clamp 32 is a conventional DC gear motor driven by a four-transistor bridge. The drive control system uses pulse-width modulation. In addition, multiple safety systems exist within the motor drive circuitry. For example, the motor current is electronically limited; a detected "failsafe" error cuts off all four legs of the bridge, thus disabling the motor; and false drive data (e.g. processor "hang" or loss of motor pulses) trips the "failsafe" subsystem.

Motor pulses are modulated by a Proportional Integral-Differential control algorithm. There are two drive encoders. The first is a rotary encoder built into the gear motor. The second encoder is a Hall-Effect pair that detects rotation of the lead screw assembly.

Referring to FIG. 2, the internal circuit of infusion pump 10 includes a master microprocessor (Master μP) 40 and a slave microprocessor (slave μP) 42 that function as a multitasking system with preemptive scheduling. Master processor 40 is primarily dedicated to operating the pump motor through a motor control module 53. As a background task, Master processor 40 performs a continuous check of ROM (read only memory) integrity and periodically checks critical RAM data areas. Slave processor 42 checks Master processor 40 in several areas. It verifies that Master processor is controlling the motor to the intended rate within tolerance limits. It performs "watchdog" checks on system activity, including timekeeping. And it checks the motor armature shaft encoder output against the lead screw's Hall Effect sensor.

(In FIG. 2 note that multiple signal lines are identified by heavy lines and single signal lines are identified by thin lines.)

Three types of memory are employed. A volatile RAM 44 contains program data. A nonvolatile ROM 46 stores the pump operating system (i.e., the firmware). And an EEPROM 48 holds the electronically loadable customized drug library 59 and supplementary configuration data, calibration information 63, as well as an event log 61 recording data gathered about the operation of pump 10.

Pump 10 includes a programmable peripheral interface (PPI) 41 that functions as a port expander for master microprocessor 40. PPI 41 manages input from keyboard 43 and several of a collection of sensors 52.

The full collection of sensors 52 includes: a syringe barrel detector, a syringe barrel diameter sensor, a syringe barrel flange detector, a plunger position sensor, a strain gauge, two Hall effect sensors and a mercury switch.

The syringe barrel detector is a series-connected, pressure-activated switch pair, built into the barrel clamp cradle. Both switches are closed only when the barrel is centered in the "V" shaped cradle and the barrel clamp slider is pressed down over the barrel of the syringe.

The syringe barrel diameter sensor is a linear-displacement potentiometer that is built into the barrel clamp slider. Its output voltage varies in direct proportion to the syringe barrel diameter and provides an indication of the diameter of the syringe.

The syringe barrel flange detector is a switch that is built into the portion of the barrel cradle clamp that grasps the barrel flange. The syringe barrel flange is captured when the barrel clamp is closed. This detector determines whether the flange has been captured.

The plunger position sensor is a linear-displacement potentiometer, mechanically coupled to the syringe plunger driver 37. The output varies in direct proportion to the plunger driver position and is used to determine the distance the plunger has been pushed into the barrel.

The strain gauge measures the amount of force exerted on the lead screw drive mechanism, which is approximately the same as the force applied to the syringe plunger. This information is used to determine the presence of an occlusion. A pressure increase beyond a predetermined threshold that can be set in the pump configuration warns that an occlusion probably exists.

The mercury switch senses whether the pump is in a vertical or horizontal orientation. This information is used as a force correction factor, to compensate for the weight of the drive screw assembly.

Pump 10 includes an external RS232 serial port 50. The pump's ROM 46 and EEPROM 48 are loaded through this port. It is also used as a serial data port for various other applications to be described. The data and other signals which come in through serial port 50 from an external source, e.g. a laptop, a personal computer, or another external computer, first pass through a level shifter 47. Level shifter 47 shifts the levels of the signals so that they conform to the internal requirement of the pump's circuitry and then passes the level shifted signals to a buffer 49. Level shifter 47 may either be internal to the pump as is suggested in FIG. 2, or it can be provided in the form of an external adapter.

To load the pump operating system into ROM 46 or the drug library and supplementary configuration data into EEPROM 48, a voltage is asserted on a PRGM program line 51 to indicate to the microprocessor that a memory load is to take place. Executable code is loaded into RAM 44 and run from RAM 44. The executable code sends the incoming data to the appropriate locations in either ROM 46 or EEPROM 48.

Another input for data is a reservoir label line 57. This line is used to "read" the contents of the touch memory label that is mounted on the syringe.

Information from the pump is communicated to the pump operator through the previously mentioned display screen and status lights, represented in FIG. 2 by display block 45.

There is also a real time clock (RTC) 55 with a battery backup to keep the clock functioning even when the pump is turned off. Among other things, RTC 55 provides a time stamp for the record of various events that take place in the pump. The details of which events are records are described below in the section entitled "Event Log".

Figure 3:
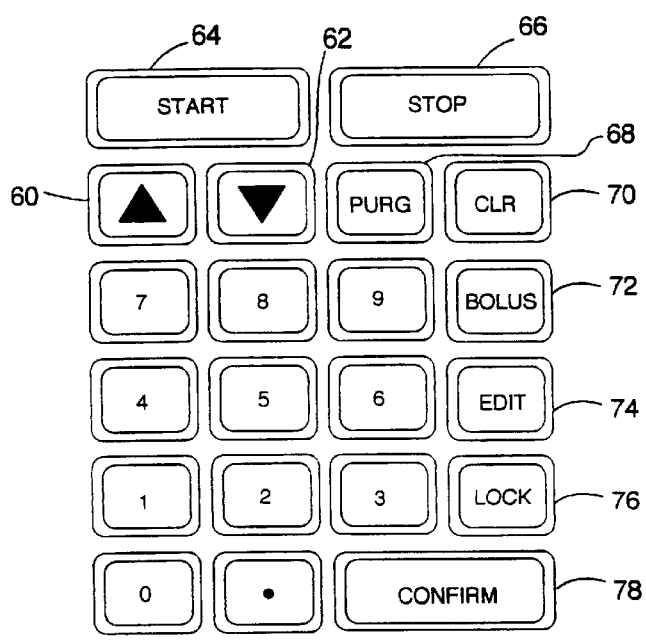
FIG. 3 shows the keyboard layout on the control panel of the infusion pump.

As shown in FIG. 3, the keyboard includes ten digit keys as well as other function keys. There are <up arrow> and <down arrow> keys 60 and 62 which are used to select, increment or decrement data. A <START> key 64 starts running a selected operation, e.g. infusing a selected drug. A <STOP> 66 key stops a running task. A <PURG> key 68 selects a purge operation. A <CLR> key 70 resets a field to its default value. A <BOLUS> 72 key selects a bolus operation. An <EDIT> key 74 enables the user to alter a previously programmed field. A <LOCK> key 76 selects and deselects the lock function, i.e., it locks out all other keys on the keyboard. And a <CONFIRM> key 78 completes a program step or displays hidden data during a run state (i.e., when pump is infusing a drug).

Figure 4:
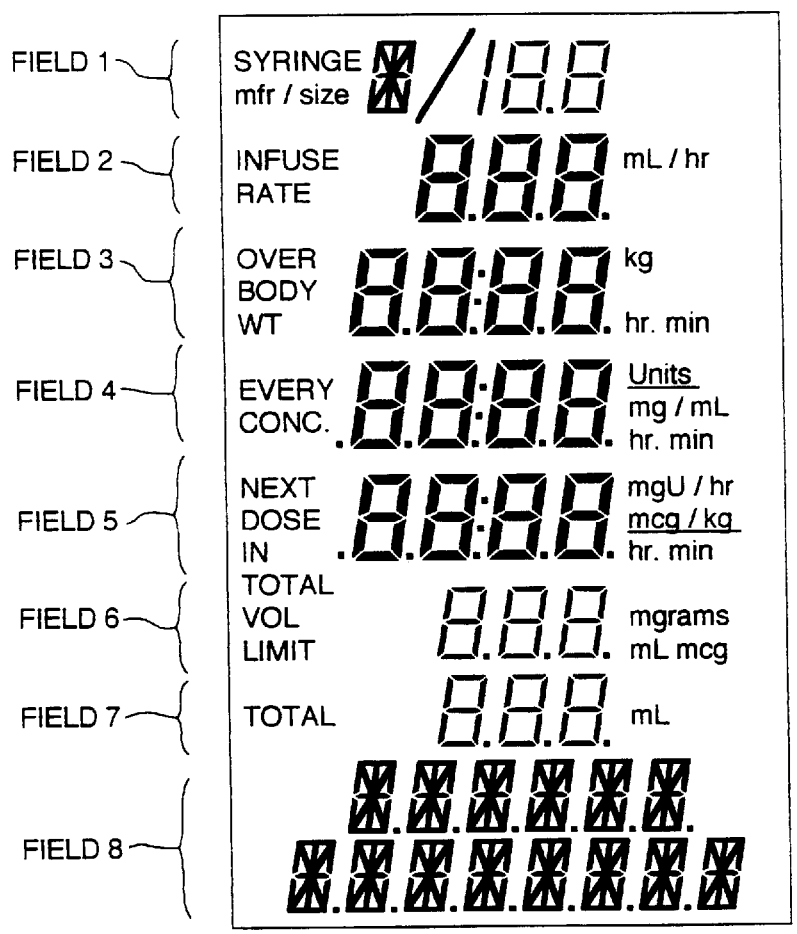
FIG. 4 is a view of the pump's display screen with all LCD segments activated.

As shown in FIG. 4, the display that appears on the LCD screen is divided into eight fields, each of which is dedicated to a certain category or certain categories of information. Field 1 displays the syringe manufacturer code and the nominal syringe size in milliliters. The single-character text sub-field within field 1 is also used to display operator responses to configuration prompts.

Field 2 displays the quantity of drug that is to be infused (mL), infusion rate (mL/hr), or bolus size (mL). Field 3 displays dose duration (hr:min) or patient body weight (kg). Field 4 displays the dose interval (hr:min), drug concentration (in mg/mL or Units/mL), or bolus size (Units). Field 5 displays the time remaining until the next dose is due to begin (hr:min) or the dose (mcg/min, mcg/kg/min, or Units/hr), or bolus size (mg or mcg/kg). Field 6 displays the total delivered (mL, mcg, mg, or grams), volume limit (mL), or bolus size (mL). Field 7 displays the total amount of fluid delivered (mL). And field 8 is a two line field that displays text prompts.

Figure 5:
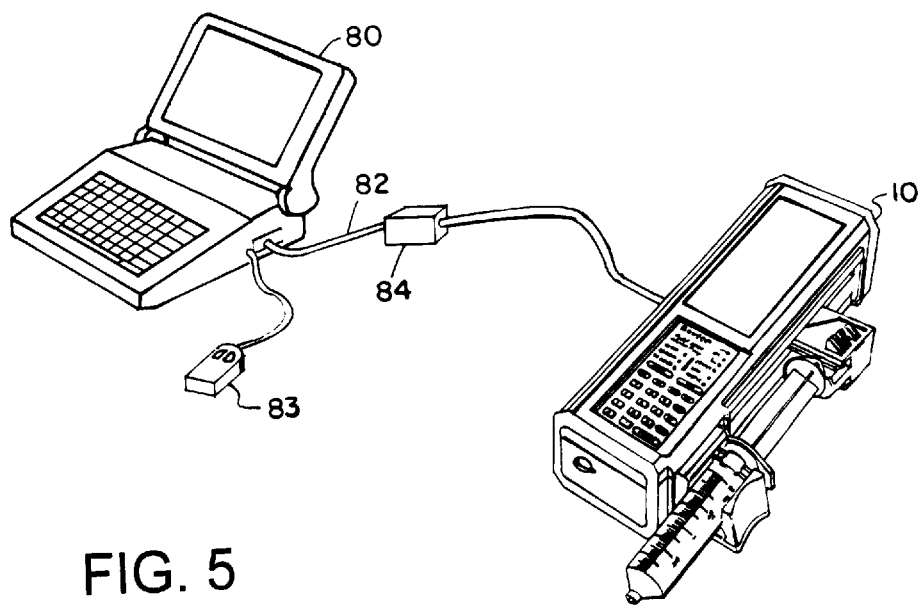
FIG. 5 shows a personal computer connected to a drug infusion pump for transferring information from and to the pump.

The Computer Interface Program:

Referring to FIG. 5, a user can electronically load a customized drug library and supplementary configuration data into a pump 10 from an external computer source, which in the described embodiment is a personal computer 80. PC 80 is connected to pump 10 through a connector cable 82 that may include an externally powered adapter 84, which performs whatever signal level shifting is required to enable PC 80 and pump 10 to communicate with each other. For example, in the described embodiment for safety reasons the 12 volt signals from the RS232 port of the PC are not permitted into the pump. Thus, adapter 84 shifts the levels of the RS232 signals prior to passing them to pump 10. In the reverse direction when information is downloaded from the pump to the PC, adapter 84 shifts the levels of the pump signals so that they conform to the requirements of the RS232 port. PC 80 also includes a mouse 83 which can be used in operating the computer interface program and/or a graphical tool that is available through the computer interface program (to be described below).

Figure 6:
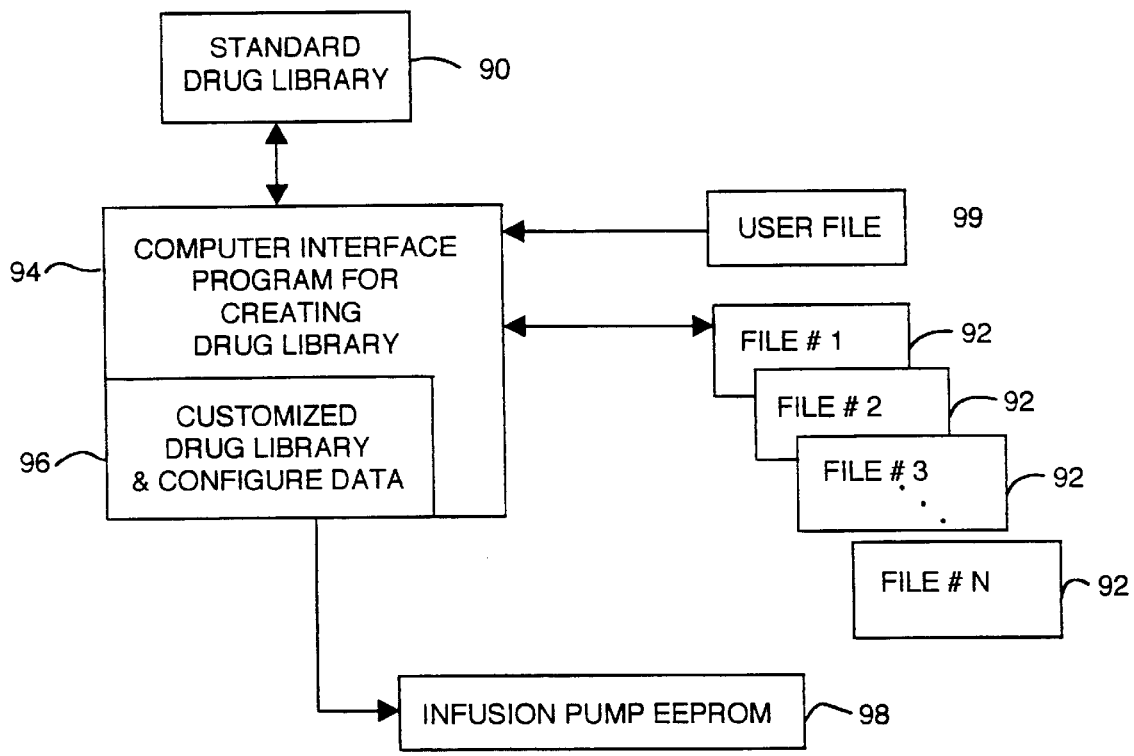
FIG. 6 is block diagram of the user interface that enables a user to load a customizable drug library and supplementary configuration data into the pump's EEPROM.

Referring to FIG. 6, the PC includes in its memory or on disk storage a standard drug library 90 containing drug delivery information for a set of drugs. The standard drug library is stored as an encrypted file. The set of drugs within the standard drug library is selected to be representative of the range of drugs that care providers from a wide variety of communities might wish to use in their own facilities. The PC includes a software application program 94 providing a computer interface that enables an authorized individual (i.e., one with authorized password and access level) to generate drug configurations specific to that user and which might include drugs not found within the standard drug library. Such user-generated drug configurations may then be stored as separate files 92. Computer interface 94 thus enables the authorized user to easily construct a customized drug library 96 both by selecting particular drug entries from the standard drug library 90 and by creating custom drug entries. Once the customized drug library has been constructed, computer interface 94 enables the user to download the customized drug library and supplementary configuration data into one or more drug infusion pumps 98 that are to be used in a particular medical facility for which the customized library was designed.

The media on which the standard drug library is stored also contains a user file 99 that contains the full name, password and authorized access level for each individual that is authorized to access the functionality of the user interface. The way in which the system uses the information stored in the user file is described below in the section titled "Security Features".

Figure 7:
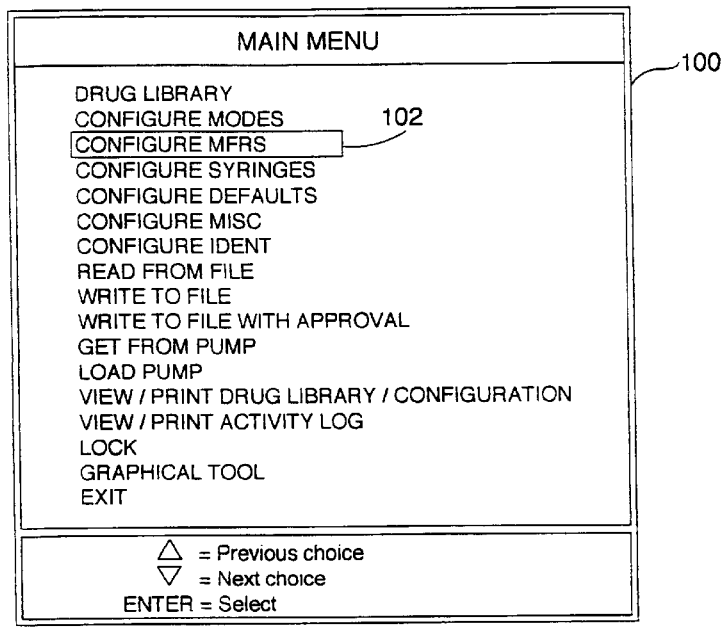
FIG. 7 shows a Main Menu screen.

Referring to FIG. 7, when computer interface program 94 is executed, it displays a Main Menu 100 on the screen of the PC. The Main Menu identifies as possible menu selections all of the functions which can be invoked through the computer interface program. (Note that the highlighting is illustrated in FIG. 7 by a box 102 enclosing the menu pick.) Users select an option by first highlighting that option and then pressing <ENTER> to execute their choice. The location of the highlighting can be moved through the options by either using the cursor keys or another cursor control device such as a mouse. The up arrow key moves up through the menu and the down arrow key moves down through the menu. In each of the menu screens that are be described below, the selections of the available options are made in a similar way.

Each of the options that are available through the Main Menu will now be described in the order in which they are shown in FIG. 7.

Either to select a drug entry from the standard drug library or to generate a drug entry not available in the standard drug library, the user first selects the "Drug Library" menu pick. In response, the program presents the user with the screen shown in FIG. 8. The top half of the screen presents a window into the current drug library, which includes all of the drug entries in the standard drug library as well as drug entries which the user can create. By using the up/down arrow keys, the user can scroll through the entries in the current drug library one at a time and in alphabetical order, each drug entry appearing in the top half of the screen. As a drug entry is being displayed, the user can then either select/deselect that entry or modify it and thereby generate a new drug entry.

Figure 8:
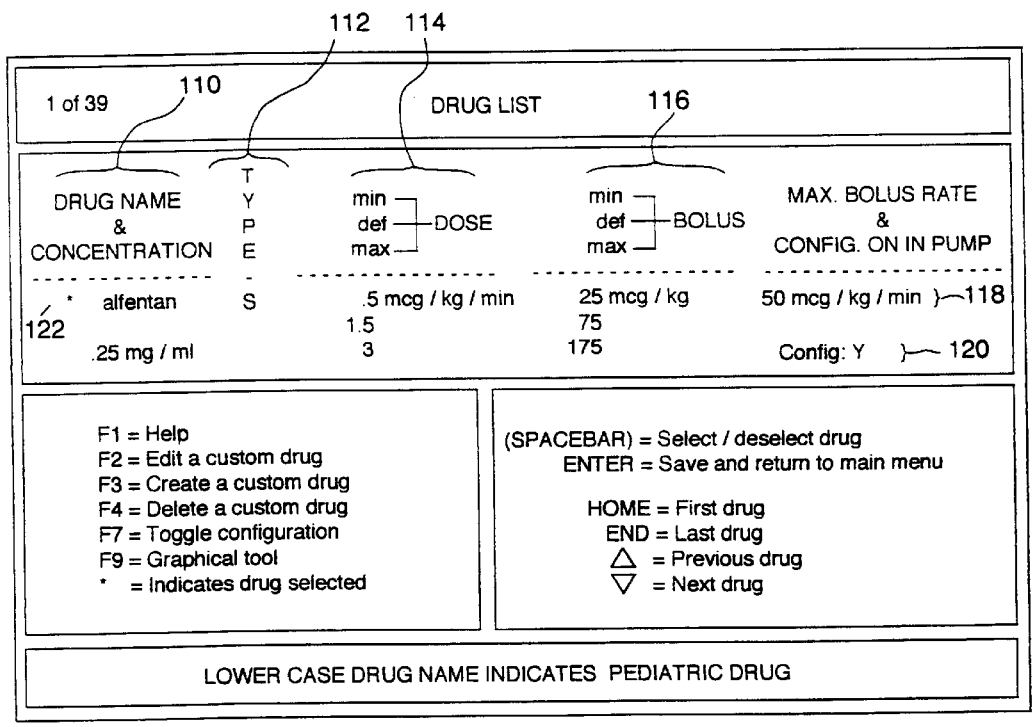
FIG. 8 shows a Drug List screen that is accessible through the "DRUG LIBRARY" menu pick on the Main Menu.

The template for each drug entry has six fields identified in FIG. 8 as fields 110–120. Field 110 identifies the name of the drug entry and the concentration. Field 112 identifies whether the drug entry is a standard drug entry found in the drug library. If the drug entry was selected from the standard drug library, this field will contain an "S". On the other hand, if the drug entry was created by the user, this field will contain a "C". Field 114 specifies the minimum, default and maximum dose delivery rates for the drug. Field 116 specifies the minimum, default and maximum bolus sizes for the drug. Field 118 specifies the maximum bolus rate at which the bolus can be delivered. And field 120 specifies whether the drug will appear on the drug selection menu within the pump. If field 120 contains a "Y", it will appear on the list of active drug entries which are available to the user of the pump. If field 120 contains a "N", then even though the drug entry is part of the customized library that was loaded into the pump, it will not be visible to the user and thus the user will not be able to select it. To change the status of a drug entry within the customized drug library in the pump, the user can enter a special editing mode in the pump and activate or deactivate any of the drug entries in the library.

The particular drug entry shown in FIG. 8 is alfentan. If the user wishes to select this drug entry to be included in the customized library that is to be loaded into the pump, the user merely presses the spacebar. The entry may be deselected by pressing the spacebar a second time. If the drug entry has been selected, this is indicated by an asterisk "*" appearing to the left of the drug entry name (see location 122).

To create a custom drug entry, the user presses F3 while the Drug List screen is being displayed. The program replaces the view of an entry in the drug library with an empty template, as shown in FIG. 9. The fields which were previously filled with information now contain dashes indicating locations in which the user can enter his own data. After entering the name of the drug entry for which delivery information will be entered, the user moves to the other fields to supply the desired rate information. Repeated presses of the TAB key moves the user through the fields one at a time. In all fields, data is entered in the usual manner through the keyboard. By pressing F5 when in this screen, the user can move through the available drug delivery modes (i.e., mL/hr, mcg/hr, Units/hr, mcg/kg/min, etc.) and choose the desired mode for representing the drug delivery rate information. Certain fields may be left empty. For example, the bolus information can be left blank. When the pump operator attempts to administer a bolus for this drug, the pump will declare that as an invalid operation and not permit it.

To edit a custom drug entry, the user presses F2. The user is then allowed access to the existing custom drug entry's fields and can edit the contents of those fields.

FIG. 10 shows the "Create/Edit A Custom Drug" screen after the user has entered drug delivery information for a fictitious drug called "New Drug". In this example, notice that the user selected the drug mode mcg/min.

The selection of the "Create/Edit a Custom Drug" function automatically identifies the new drug as selected so that will be active when downloaded into the infusion pump. In other words, it is assumed that the user is generating a drug that is to appear in the customized drug library. If the user wishes to "hide" the drug, this is done by simply deselecting the drug after returning to the "Drug List" screen.

Figure 11:
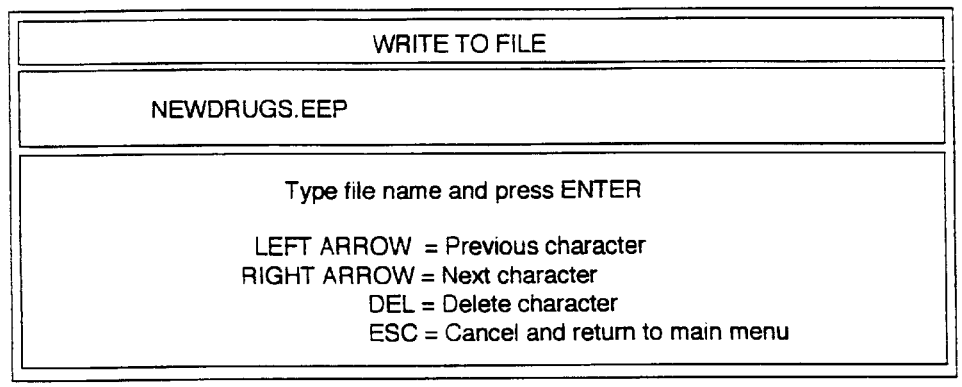
FIG. 11 shows a Send Configuration to File screen that is accessible through the Main Menu.

After the user has specified the contents of the customized drug library, the user can return to the Main Menu from the Drug List screen by pressing <ENTER>. From the Main Menu, the user can save the drug selections and supplementary configuration data to a file by selecting "WRITE TO FILE". In response, the program displays the screen shown in FIG. 11 and prompts the user to name the file. After entering the file's name, another press of the <ENTER> key causes the program to perform the save function.

From the Main Menu, the user can further configure the pump by specifying the modes that will be available, the syringe manufactures that the pump will recognize, the syringe sizes that it will recognize, the defaults used by the pump, and other miscellaneous features. This is done with the aid of the other CONFIGURE functions that appear on the Main Menu. Each of the configure functions will now be described.

Figure 12:
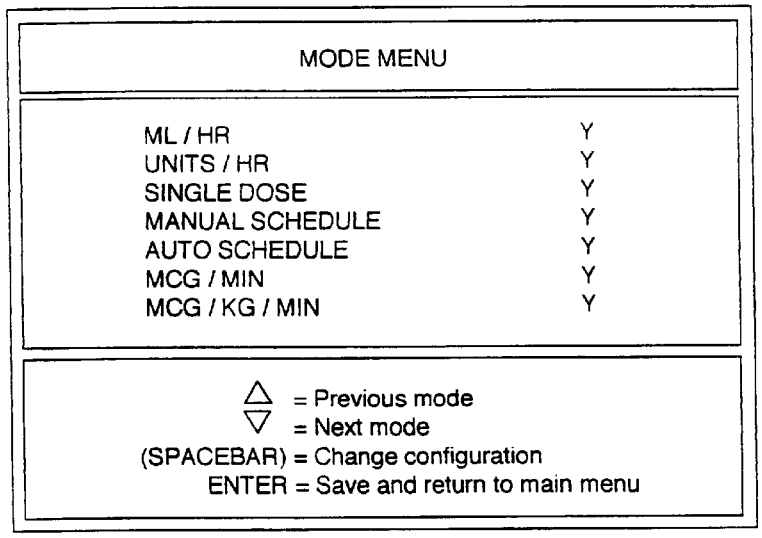
FIG. 12 shows a Mode Menu screen that is accessible by selecting the "CONFIGURE MODES" option in the Main Menu.

When CONFIGURE MODES is selected, the program displays the MODE MENU screen shown in FIG. 12. There are seven modes which can be activated/deactivated from this screen. The configure modes allow the user to determine which modes will be available in the mode selection step of pump programming. The choice of mode typically depends upon the type of drug being administered as well as the particular convention that has been adopted by the care facility or medical community using the pumps.

The modes define the way the user is to specify the drug delivery information. They are: ML/HR, UNITS/HR, MCG/MIN, MCG/KG/MIN, SINGLE DOSE, MANUAL SCHEDULE, and AUTO SCHEDULE. Of course, these specific mode options are merely representative of a much larger range of choices that one might wish to make. The chosen set of options would likely depend in part on the local customs of the medical community using the infusion pumps.

Figure 13A:
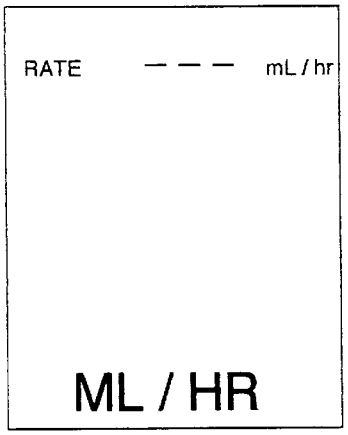
FIGS. 13a–g show the screens that are displayed on the pump for the different drug delivery modes.
Figure 13B:
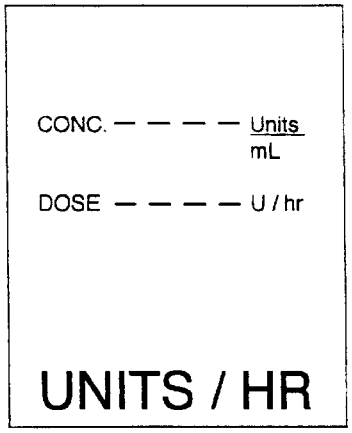

In the mL/hr mode, illustrated by the screen shown in FIG. 13a, the user specifies the drug delivery rate directly. In the units/hr mode, illustrated by the screen shown in FIG. 13b, the user specifies the concentration of the drug in units per ml and the desired dose in units per hour. From those two pieces of information, the pump then calculates a rate in mL/hr. In mcg/min mode, illustrated by the screen shown in FIG. 13f, the user specifies the concentration of the drug in the syringe (in mcg/mL) and the desired drug dose rate (in mcg/min). The pump then calculates the rate at which it must deliver fluid from the syringe. In the mcg/kg/min mode, illustrated by the screen shown in FIG. 13g, the user specifies the concentration of the drug in the syringe, the weight of the patient and the desired dose/kg/min for that drug. The processor in the infusion pump computes the rate at which the pump must deliver fluid from the syringe.

Figure 13C:
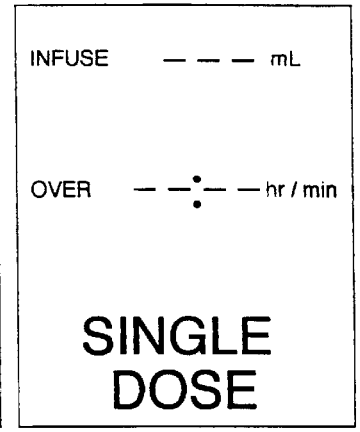

In SINGLE DOSE mode, illustrated by the screen shown in FIG. 13c, the user specifies a volume to be delivered and a time in which it is to be delivered. For example, the user may specify 5 mL of drug to be delivered over a period of 4 hours. The pump then computes the rate at which the syringe will deliver the drug.

Figure 13D:
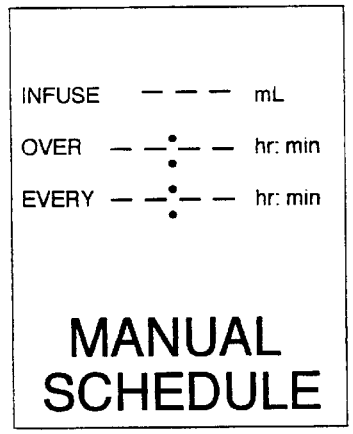
Figure 13E:
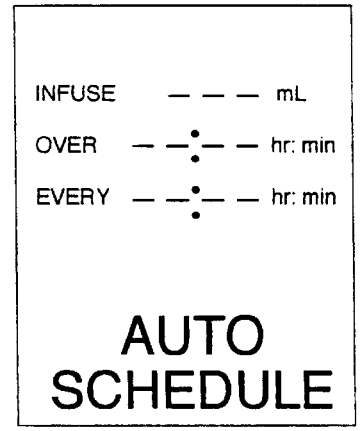
Figure 13F:
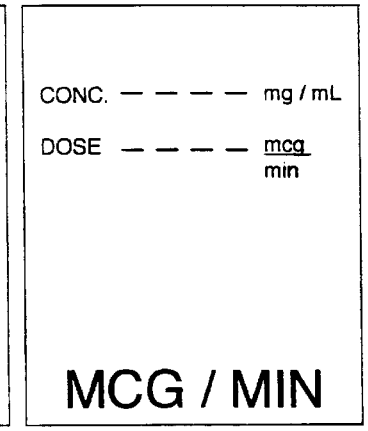
Figure 13G:
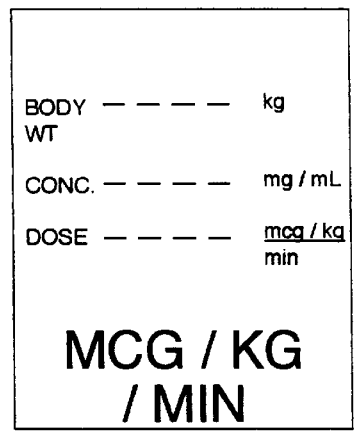

In MANUAL SCHEDULE and AUTO SCHEDULE modes, illustrated by the screens shown in FIGS. 13d and 13e, respectively, the user specifies a volume to be delivered, a time over which it is to be delivered, and a repeat time. Thus, for example, the user might specify 4 mL to be delivered over one hour every 8 hours. The difference between manual schedule and auto schedule is that in manual schedule mode when it is time for the next dose, the pump alarms and the user must manually start the dose. In auto schedule, the next dose starts automatically at the scheduled time.

Mode selection/deselection is done by highlighting the mode and pressing the spacebar. After all of the mode selections are specified, pressing the <ENTER> key causes the program to save that information and return to the Main Menu.

Figure 14:
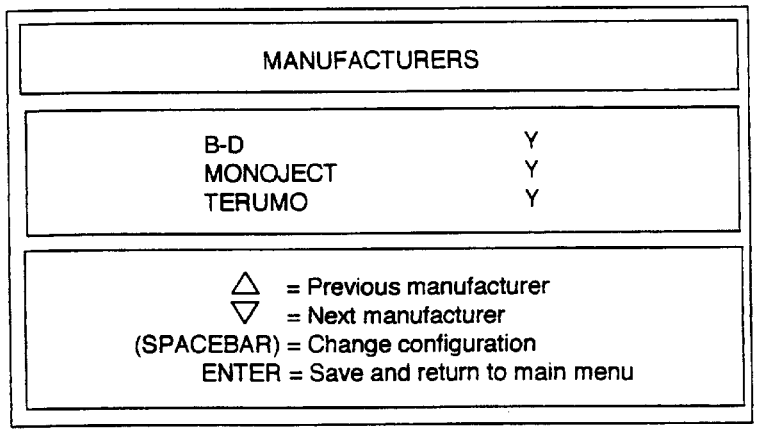
FIG. 14 shows a Manufacturers screen that is accessible by selecting the "CONFIGURE MFRS" option in the Main Menu.

When CONFIGURE MFRS is selected in the Main Menu, the program displays the screen shown in FIG. 14. Through this screen, the user can identify manufacturers of syringes that can be used in the pump. Note that the pump must know the manufacturer of the syringe in order to determine the syringe size. It includes tables of barrel sizes that correspond to specific manufacturers and to specific syringe sizes used by that manufacturer. In order to recognize the syringe size, the pump must know the manufacturer of the syringe so it can use the correct table to convert barrel size to syringe size. In the described embodiment, there are three manufacturers that the pump recognizes, namely, 1) MONOJECT=Monoject®
2) B-D=Becton Dickinson Plastipak®
3) TERUMO=Terumo®.

As described above, pressing the spacebar selects/deselects the different choices and pressing the <ENTER> key saves the results before returning the user to the Main Menu.

Referring again to FIG. 7, from the Main Menu, the user can also select CONFIGURE SYRINGES. In response, the program displays the Syringes Menu shown in FIG. 15. This menu presents a list of all the syringe sizes that the pump can recognize for each manufacturer that it can recognize. By using the <spacebar>, the user can select/deselect the desired sizes. If the configuration information that is downloaded to the pump does not specify a syringe of a particular size, the pump will not be able to recognize or allow selection of that syringe size and it cannot be used in the pump.

Many hospitals deal with only one syringe manufacturer. For example, the hospital may only use B-D syringes. The person who program the pumps for that facility may wish to select only that manufacturer and turn off the other two. At the pump programming step when the pump would normally prompt the user to select the manufacturer, it would instead prompt the user to verify B-D. The user would verify B-D by simply pressing <CONFIRM>.

From the Main Menu, the user can select CONFIGURE DEFAULTS. In response, the program displays the Defaults Menu shown in FIG. 16. There are four default categories, namely, drug default, mode default, manufacturer default and syringe default. If the drug default option is selected, when the select drugs step in the pump prompts the user to press an up or down arrow key, the first up or down arrow key cause the pump to display the last drug that was run in the pump. Note that the user has to begin a bolus or infusion to record the default settings for the next time the pump is turned on. The pump records what drug (if any) is being used, what mode is being used, what syringe manufacturer is being used, and what syringe size is being used. Then, if any of the corresponding default options are set, these recorded settings will be the first choices presented to the user when the pump is next turned on.

Another configuration option available through the Main Menu is CONFIGURE MISC. When this option is selected, the program displays the Miscellaneous Feature Menu shown in FIG. 17. Each of the options available through this menu will be described in the order in which it appears.

Drug Library Enable determines whether the customized drug library that is loaded into the pump will be directly accessible when the pump is turned on. If Drug Library Enable is not selected, the customized drug library is present in the EEPROM of the pump but in normal operating mode the pump does not appear to have a drug library stored within it. It operates as if the drug library feature does not exist and the pump does not prompt the user to select a drug. The user can, however, enable the drug library in the pump by entering configuration set mode in which the user can toggle the Drug Library Enable setting.

Syringe Recognition is a convenience feature that simplifies programming by initializing the "SYRINGE size" field to the size of the syringe that is mounted. If Syringe Recognition is enabled, the pump automatically identifies the size of the syringe that is inserted into the pump. If Syringe Recognition is turned off, the pump does not recognize syringe size.

If both syringe recognition and syringe default are turned on, regardless of what the syringe default is, the syringe recognition function takes precedence. Thus, if the user previously ran a 5 ml syringe last and then mounts a 30 ml syringe, the pump will recognize it as a 30 ml syringe.

Syringe Detection is a safety enhancement that enables the pump to issue an alarm if the syringe is improperly mounted in the barrel clamp. This feature is active even while the pump is delivering. Syringe Detection is automatically configured when Syringe Recognition is enabled. A group of three switches is used to perform the detection function. Two of the switches are in the barrel clamp and one switch is in the part that captures the flange of the syringe. When Syringe Detection is enabled, if any of the switches fails to detect the presence of a syringe in the pump when an attempt is made by the user to start motor movement, the pump will display a "Load Syringe" or "Check Syringe" message to the user and will not initiate motor movement.

PSI Range enables the user to select the pump's sensitivity for detecting occlusions. There are three possible settings: low, medium or high. The pump includes a strain gauge which measures the force exerted on the syringe by the plunger driver. If the force exceeds a preselected threshold determined by PSI Range, an alarm sounds indicating the presence of a possible occlusion. The alarm will trigger at a lower force for a low setting as compared to a high setting.

Rate Range limits the maximum fluid delivery rate. It too has three possible settings, low, medium, and high. These settings place an upper limit on how fast the pump can deliver the fluid from the syringe. The high setting allows the pump to deliver up to 360 mL/hr. The medium setting has a limit of 120 mL/hr. And the low setting has a limit of 15 mL/hr. This feature prevents the user from accidentally programming the pump to too high a rate. The rate range setting applies severally to bolus, purge, and infusion rate.

Auto Lock is a feature that locks the keyboard automatically after two minutes if there is no activity on the keyboard. This provides protection against inadvertent activation of a key.

The Volume Limit feature is a special feature for the mL/hr mode only. It enables the user to set a limit upon how many milliliters of drug will be delivered. Whenever that limit is reached, the pump stops and alarms.

The Silent Running features enables the user to eliminate the audio component of certain warnings that are provided by the pump. For example, the pump will issue a warning when there is only 10 minutes left before the syringe will be empty. If silent running is enabled, the audio portion of this alarm will be suppressed. This feature is for use in areas in the hospital where the provider does not want to disturb the patient unnecessarily.

The Idle Alarm feature controls the type of signal that is issued when the pump's keyboard has been idle in stand-by state for two minutes continuously. Normally, the pump will issue a warning of 15 beeps, and repeat that warning every two minutes that the keyboard remains idle. When the Idle Alarm feature is enabled, the pump will beep repeatedly until a key is pressed.

Referring again to FIG. 7, if the user selects "CONFIGURE IDENT", the screen shown in FIG. 18 appears and the user is prompted to enter an identifier that will be displayed in the pump LCD following the power-on lamp test. This can be used, for example, to identify the particular configuration that has been loaded into the pump or the identity of the intended user of the pump. By selecting "WRITE CONFIGURATION TO FILE", the user can save the customized drug library and configuration information to a file on the PC. Later, by selecting "READ CONFIGURATION FROM FILE", the user can read a selected configuration file into active memory on the PC for review or further editing.

To load a configuration into the pump, the user ensures that the pump is properly connected to the PC and turned on. The user selects the "LOAD PUMP" option, and the program then downloads the configuration into the pump's EEPROM.

The program also enables a user to read the drug library and supplementary configuration data from the EEPROM. To do so the user selects the "GET FROM PUMP" menu choice. This function reads not only the drug library and supplementary configuration data that had been previously loaded but also operational information that has been collected buy the pump as well as any changes to the configuration that have been entered by the user through the pump's special editing capability. (The details of what information is collected by the pump are described below.)

Still referring to FIG. 7, the program also enables the user to view the full customized drug library and supplementary configuration data by either displaying it on the screen of the PC or by sending it to a printer.

The "Lock" pick in the Main Menu allows the user to leave the computer interface program running on the PC and prevent unauthorized use of the program's functions while the user is away from the computer. The PC will not allow further access to the computer interface program's functions until the current user's password is reentered.

The Graphical Tool

The computer interface program also provides a convenient graphical tool for selecting the appropriate concentration and syringe size for a given drug. Each drug has associated pharmacodynamic (clinical) data having to do with the effects of the specific drug on a particular class of patients. From this data, a minimum, default, and maximum dose and bolus rates can usually be derived. The range from minimum dose to maximum dose defines the therapeutic range of the drug, i.e., the dose range over which the drug should generally be used to effectively achieve the intended therapeutic effects.

It is important to select the appropriate drug concentration for the class of patients to which the drug will be administered. If the drug delivery mode is mcg/kg/min, the rate of fluid delivery is a function of both the weight of the patient and the concentration of the drug in the syringe. If the drug is being delivered to a heavy patient and the concentration is low, the fluid flow rate required to achieve the specified dose can be quite high. This may mean that the syringe that is selected will not last very long and multiple syringe loads will be necessary. That would be undesirable. On the other hand, if the patient is a child (i.e., low weight) and the concentration is high, the fluid flow rate required to achieve the specified dose may be so low that it is outside the range of safe and effective operation of the pump. For example, the time required to detect an occlusion (i.e., the time to achieve the threshold pressure) may become so long that the occlusion detection system is ineffective. In addition, when fluid flow rate is very low, the transit time required for the drug to traverse the tubing connecting the pump to the patient may become unacceptably long. These too are undesirable outcomes.

Figure 20:
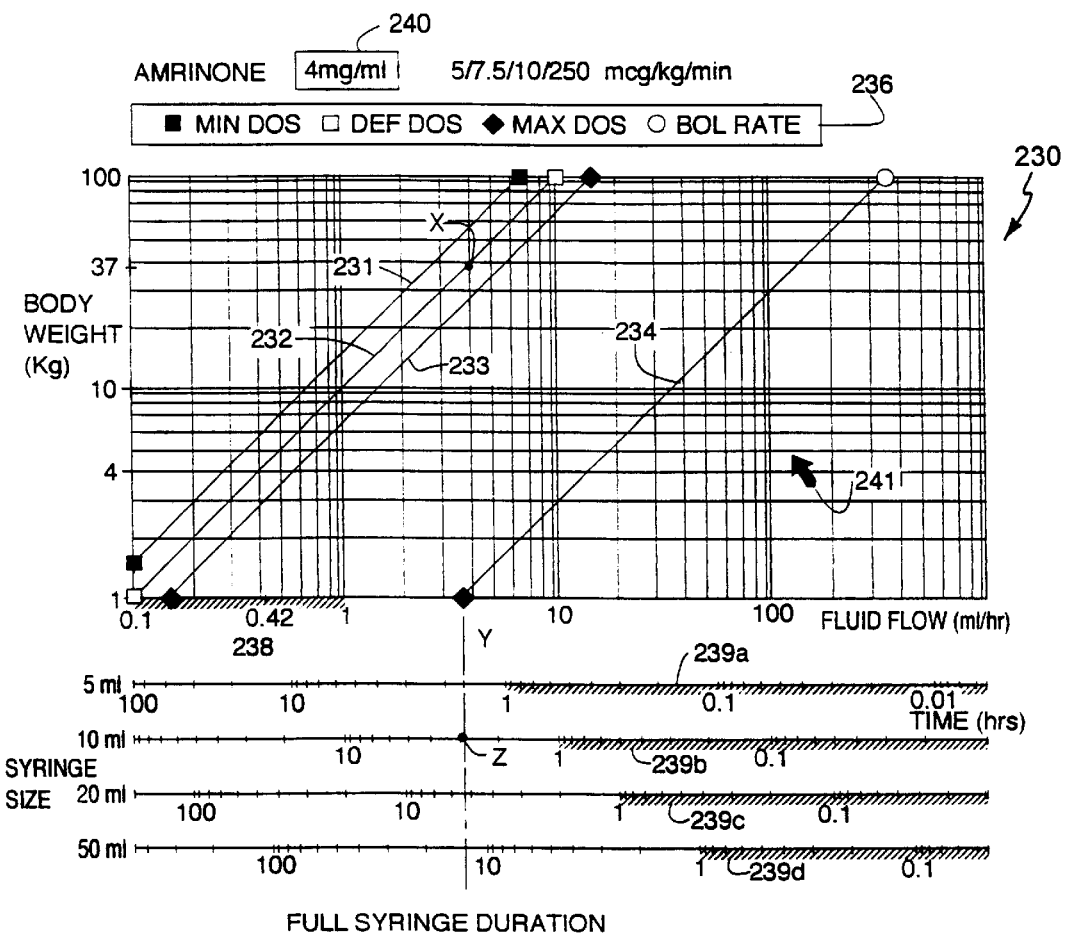
FIG. 20 shows a display screen generated by the graphical tool.

To select the drug concentration appropriately and without error can be difficult. The graphical tool that can be invoked through the Main Menu (see FIG. 6) or from a Create/Edit A Custom Drug Menu (see FIG. 9) greatly simplifies the selection of an appropriate drug concentration. When the graphical tool is invoked, the screen shown in FIG. 20 appears on the display. The upper region 230 is a log—log graph displaying body weight along the y-axis (i.e., vertical axis) and fluid flow rate along the x-axis (i.e., horizontal axis). The lines 231, 232, 233, and 234 are a plot of the following equation $$\text{Body Weight} = \frac{\text{Rate} \times \text{Concentration} \times 1000}{\text{Dose} \times 60},$$

for different doses (i.e., minimum, default, and maximum doses and bolus dose rate, respectively) and a given concentration. Since the curves are plotted on a log—log graph, the equation for those curves becomes:

Log(Body Weight)=Log(Rate)+$K$, where K is:

$$K = \text{Log}\left(\frac{\text{Concentration} \times 1000}{\text{Dose} \times 60}\right).$$

One can readily see that the displacement of the curves depend upon the concentration and the desired dose (or bolus).

Below the graphical representation are four horizontal axes, each one corresponding to a different syringe size. Each axis indicates the amount of time a syringe of that size will last if it delivers fluid at the rates shown at the corresponding locations on the fluid flow axis of the graph. Shaded regions 238 on the fluid flow axes and shaded regions of the syringe size axes 239*a–d* represent undesirable operating regions. Operating in shaded region 238 on the fluid flow axes is undesirable because the sensitivity for detecting an occlusion is unacceptable. A flow rate which falls within region 238 would result in undesirably long delays in detecting an occlusion or excessively long catheter transit time. Operating in shaded regions 239*a–d* on the horizontal axes for the different syringe sizes is undesirable because this would require frequent and multiple syringe loads. These, regions can, of course, be adjusted to reflect the preferences of the user.

The illustrated example is for the drug Amrinone with a concentration of 4 mg/ml and min/def/max doses of 5/7.5/10 mcg/kg/min and a bolus dose rate of 250 mcg/kg/min. The curves are tagged to identify which curve corresponds to which dose and a legend 236 indicates which tag corresponds to which dose. On a color display other possibly more effective ways could be used to identify this mapping of curves to dose. For example, a color coding scheme could be used.

From this graphical representation, the user can determine whether the selected concentration is appropriate for the body weights of patients that will likely be receiving the drug and the syringe sizes that are available.

An example will help illustrate how the graphical display is used. Assume that the typical body weight is 37 kilograms. This body weight intersects the default dose curve at the point labelled "X", which, in turn, corresponds to a fluid flow rate of about 4.2 ml/hr for a drug having a concentration of 4 mg/ml (see the point labelled "Y"). At this fluid flow rate, a 10 ml syringe will last 2.6 hours (see point labelled "Z"). Also note that the fluid flow rate X falls in none of the shaded regions 238, or 239*a–d* thereby indicating that the occlusion detection sensitivity would be acceptable and fluid flow rate is not too high.

If, on the other hand, for purposes of illustration, the body weight was 4 kg, the resulting fluid flow rate for the default dose would be about 0.45 ml/hr. This level falls well with shaded region 238 and thus would be considered to be too low. To move the rate up to an acceptable level, one must decrease the drug concentration. Note that a decrease in the drug concentration will move the set of curves (i.e., curves 231, 232, 233, and 234) to the right in the graph. The program permits the user to change the concentration in two ways. The user can enter a new drug concentration in field 240 and see whether the fluid flow rate resulting from the new concentration falls within the acceptable region. This approach will likely require that the user make several estimates of the drug concentration until arriving at the desired outcome.

The program also permits the user to determine the appropriate drug concentration by "dragging" the set of curves to the location on the graphical display that will yield the desire fluid flow rate. To do this, the user moves the cursor 241 over to the set of curves, captures any one of the curves, drags it to the desired location, and releases it. With the curves at the new location, the program computes the concentration that would be required to achieve that location of the curves. The program does this simply by computing a new value for K, the offset coefficient for the curves.

Dragging can be performed either by a mouse which is attached to the PC or by the cursor keys on the keyboard of the PC. In addition, since it is desirable to have concentrations of integer amounts (or of discrete amounts selected from a set of available concentrations), the program only permits curves to be drawn at the permitted discrete concentration values. Thus, when the user drags the curves to a new location and releases the curves, the curves "snap" to a location representing the closest permitted discrete value for the concentration. For example, in this way, concentrations of 3.567 mg/ml are not permitted.

Security Features

The computer interface program includes several security features which are designed to prevent its unauthorized use and to prevent loading of unapproved drug library/configuration data files into the infusion pump. These features will now be described.

Access to the computer interface program itself is permitted only to persons who are identified in the user file 99 (see FIG. 6) and who provide the private password assigned to them. The user file is an encrypted disk file on the PC 80, which includes the full name of each person authorized to use the program, the password associated with each name, and the access level associated with each name.

There are five access levels, namely, supervisory, and access levels 1, 2, 3, and 4, listed in order of decreasing access rights. Each access level implicitly includes all rights conferred by the access levels below it. Picks for functions not allowed by the access level of the current user are omitted from their respective menus.

Supervisory access level allows access to the user file 99. Addition and deletion of user access records are allowed, as is alteration of any person's name, password and/or access level specification within the user file 99. Supervisory access level also allows the use of the "Write to File with Approval" pick from the Main Menu, which enables supervisory approval of a drug library/configuration data file. Without supervisory approval, a drug library/configuration data file cannot be loaded into a pump.

Access levels 1 and higher allow authorship of drug library changes through the "Drug Library" pick from the Main Menu, including the creation, deletion and editing of custom drug entries.

Access levels 2 and higher allow authorship of drug library changes through the "Drug Library" pick from the Main Menu, excluding the creation, deletion and editing of custom drug entries.

Access levels 3 and higher allow authorship of configuration data changes via the "Configure <group>" pick from the Main Menu, and allow the "Write to File" pick from the Main Menu.

Access levels 4 and higher allow the "Read From File", "Get From Pump" and "Load Pump" picks from the Main Menu. Also allowed at this access level and higher is the "View/Print Drug Library/Configuration Data" and "Locks" pick from the Main Menu.

Figure 21:
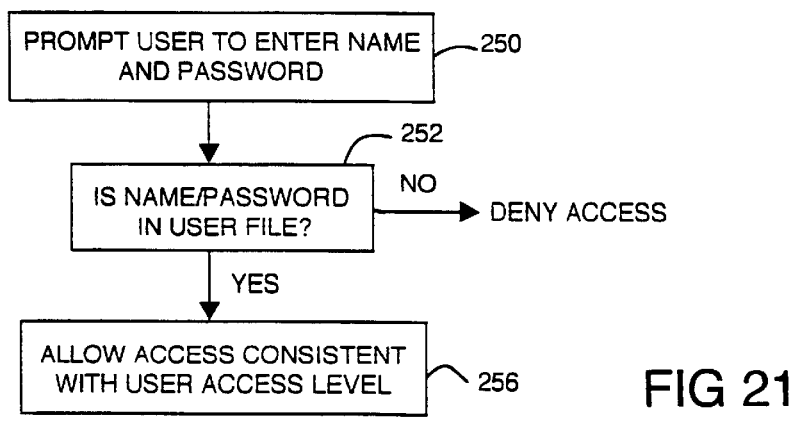
FIG. 21 is flow chart of the access security that is implemented by the computer interface program to control access to the functionality of the program

Referring to FIG. 21, when a user calls up the computer interface program, the program prompts the user for a name and password (step 250). The program then checks whether the user's name is listed within the user file 99 (see FIG. 6) and, assuming it is listed, whether the user has entered the proper password (step 252). If the name does not appear in the user file or the password is incorrect, the program denies the user any access to the computer interface program. If the user name and password are listed in the user file, the program allows the user access to the rest of its functionality consistent with the user's access level (step 256).

Figures 22, 23:
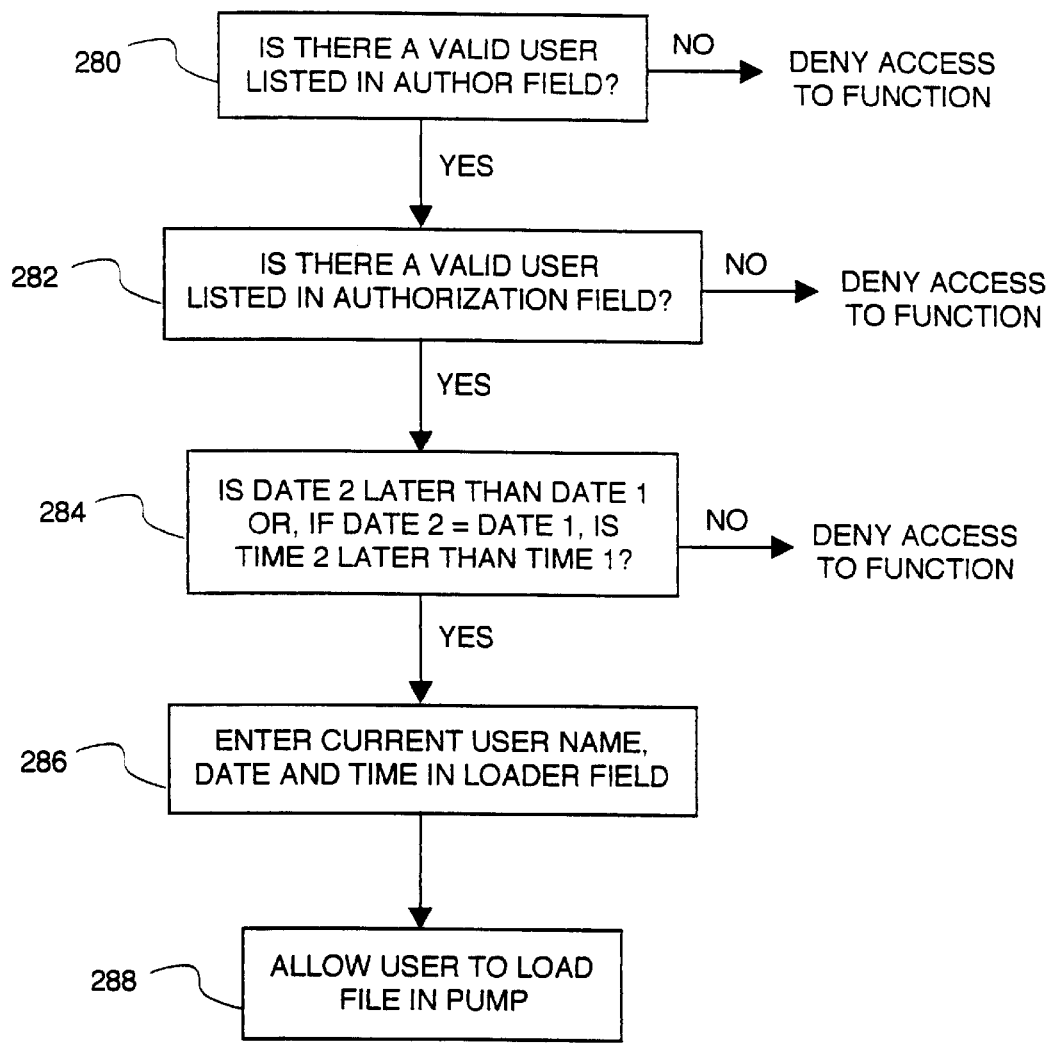
FIG. 22 shows an authorization sign-off data structure.
FIG. 23 is a flow chart of the access security that is implemented by the computer interface program to control access to the ability to load a drug library into a pump

Referring to FIG. 22, each drug library and supplementary configuration date file that any user creates, whether stored on disk or within the infusion pump, includes a data structure 260 with three name, date and time fields in it. The computer interface program uses data structure 260 to determine whether the particular drug library and supplementary configuration data file with which it is associated can be loaded into a pump. The first field (field 262) contains the identity of the author of the file. In this case, the author is defined as the last person to edit or modify the file. Author field 262 also includes the date and time of the last modification to the file. The second field (field 264) includes the name of the person who approved the file for loading into a pump. This field will only contain a name of a person who has supervisory level access as specified in the user file. Approval field 264 also contains the date and time of when the approval was given. Finally, the last field (field 266) is reserved for the identity of the person who loads the file into a pump. Like the other fields, it will also contain a date and time but in this case the event being recorded is instruction to load the file to a pump. When the file is loaded to a pump, the name of the person loading the file into the pump and the date and time are added to data structure 260. The contents of this data structure are then loaded into the pump. Thus, it is possible at a later date by reading the contents of the pump to determine who authored the pumps drug library/configuration data file, who approved it, and who loaded it into the pump.

Whenever a user creates or modifies a file, the program erases the entries in approval field 264 and updates the information in author field 262. Thus, the act of modifying a file after it has been approved for loading into a pump cancels the approval. Before that file can be loaded into a pump it must again be authorized by an appropriate person.

Referring to FIG. 7, the Main Menu includes a "Write to File with Approval" menu pick which enables a user to authorize a configuration file. This functionality can be invoked only by a person having a supervisory access level.

Referring to FIG. 23, when a user attempts to load a file into a pump by selecting "LOAD CONFIGURATION TO PUMP" in the Main Menu, the program performs the necessary checks before permitting the user to perform the loading operation. First, the program determines whether there is a valid user identified in author field 262 (step 280). If that field contains a valid user, the program checks whether a valid user having supervisory access level is identified in approval field 264 (step 282). The approval must come from a user different from the author. If the contents of the data structure fails either of the tests in steps 280 or 282, the program dose not permit the user to load the drug library/configuration data file into the pump. On the other hand, if the contents of the data structure passes both tests, the program then checks whether the approval was given after the last modification to the file (step 284). If the date in approval field 264 is later than the date in author field 262, the file passes this test. If the approval date is earlier than the date in author field 262, it fails the test. If the dates are the same, the program checks the time stamps in the two fields for which was earlier. If the file was changed after the time at which approval was given, the program returns to the Main Menu and does not allow the user to load that file. If the file received its approval after the last change to the file, the program allows the user to proceed with loading the file.

Before loading the file, however, the program updates the information in field 266 of data structure 260 with the current user's name and the current date and time (step 286). After the contents of data structure 260 have been updated to identify the person who is loading the drug library into a pump, the program loads the pump as requested (step 288).

Infusion Pump Operation

Figure 19A:
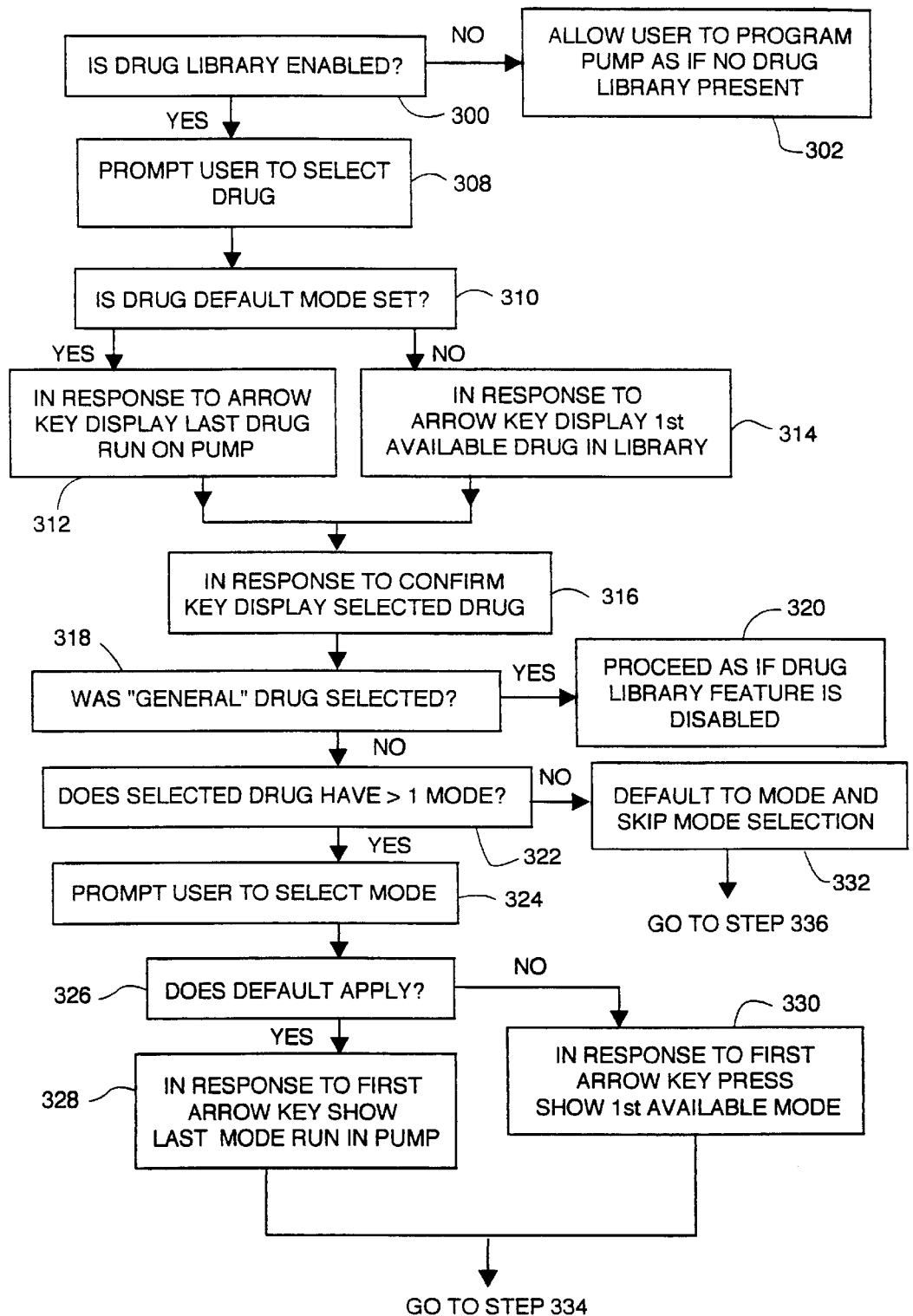
Figure 19C:
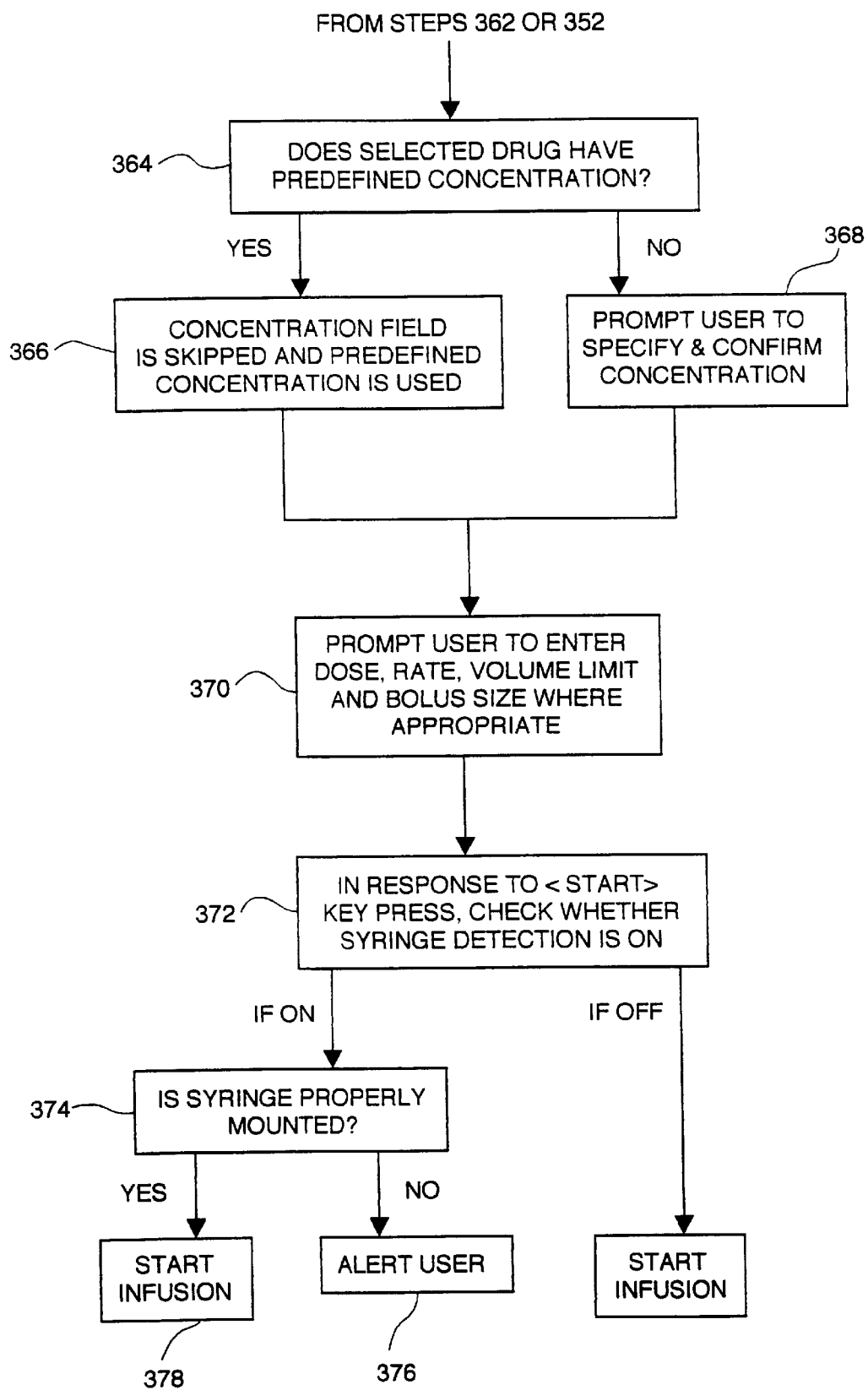

The procedure for operating the pump and using the customized drug library stored in its EEPROM to program the drug infusion pump will now be described, with the aid of FIGS. 19*a*–*c*.

The infusion pump is turned on by moving a power on switch on the side of the pump (not shown in the figures) to its "ON" position. Upon being turned on, the pump performs a power-up initialization including a self-test. The user interface portion of the self-test includes lamp and audio tests. Portions of the self-test are also performed as background tests during normal operation.

During the lamp test all LEDs and LCD segments are activated. After the lamp test, if an alphanumeric identifier has been configured, it is then displayed. After these initial steps have been completed, the pump displays the initial group selection.

First the pump checks whether the drug library feature is enabled (step 300). If the Drug Library option is not enabled, the pump proceeds as though no drug library is present (step 302). That is, the user programs the pump by entering all of the drug delivery details through the keyboard on the front of the pump. The options that are available to the user are, however, constrained by the configuration options and features that were loaded into the EEPROM from the PC. For example, if the only mode that is configured is mL/hr, then the user of the pump can only select this option when the pump is turned on (unless, of course, the user enters the configuration set mode and turns on the other mode options). The following description assumes that all modes and features are turned on.

The sequence of entries required from the user for the different modes are summarized in FIG. 24. The pump prompts the user to select a mode from among the available modes on the pump, to then identify the syringe manufacturer from among those listed in the pump and finally to specify a syringe size from among the sizes listed in the pumps memory (see row 200 in FIG. 24). After supplying those three entries, the sequence of events differs depending upon the mode that the user selected.

If the selected mode is mL/hr (column 220), the pump prompts the user to specify an infusion rate in mL/hr (row 206). Then, the pump prompts the user to enter a volume limit in mL, if one is to be used (row 208). In response to the <BOLUS> key, the pump prompts the user to enter the size of the bolus in mL (row 210). After that information has been entered, the user presses the <PURGE> key (row 212) and then the <START> key (row 214) to initiate a purge process. Following the purge, the <START> key is pressed to initiate an infusion according to the program that was entered. Since the rate is entered as mL/hr, the pump simply implements the rate supplied.

If the mode is Units/hr (column 222), after specifying the manufacturer and syringe size, the user enters the concentration of the drug that is in the syringe in Units per milliliter (row 204). Once the concentration has been specified, the user is prompted to enter an infusion dose in units/hr (row 206). Then, the user is permitted to optionally specify a bolus size in Units (row 210). At that point, the user may start the program. The pump computes the rate at which it must deliver the fluid in mL/hr and it delivers the drug at that computed rate.

If the mode is mcg/min (column 224), the user performs the same sequence of events as are performed for programming the Units/hr mode, except that the drug concentration is specified in mg/mL, the dose is entered as mcg/min and the bolus size is specified in mg. The pump computes the appropriate drug delivery rate in mL/hr.

For the mcg/kg/min mode (column 226), after syringe size is specified, the pump prompts the user to enter the patient's body weight in kg (row 202). Then, the user enters drug concentration, dose and bolus size in that order and using the units appropriate to this mode. The pump computes the drug delivery rate required to achieve the specified dose level.

Referring again to FIG. 19a, if the Drug Library option is enabled and at least one drug has been configured, the pump reads the drug library index from the EEPROM immediately following the lamp test. Depending upon how the user customized the drug library that was loaded into the EEPROM, much of, if not all of the drug delivery information, may be supplied by the drug library entry.

If an identification field is configured, the identification field is displayed during the reading of the drug library index data, otherwise the pump displays "LOADNG DRUGS".

During the process of reading the drug library index, the pump performs a checksum on the data. If the pump detects a checksum failure, a "DRUGS CORRUPT" error response is displayed to the user. After the 2 second text display, the drug selection programming step is skipped, and the pump proceeds with mode selection.

Assuming that the drug library index has been read without any detected errors, the pump prompts the user to select a drug (step 308). The user enters and moves through the list of drugs stored in the customized drug library by using the arrow keys. The <Up Arrow> key moves in the forward alphabetical direction and the <Down Arrow> moves in the reverse alphabetical direction. Where the pump enters the list of drugs depends upon whether drug default mode is set. Thus, to determine the pump's response to the user's first arrow key press, the pump checks whether the drug default is on (step 310). If the drug default is on, the first drug that is displayed is the last drug that was run on the pump (step 312). If the drug default is off, the first drug that is displayed is the first drug in the alphabetically organized drug library (step 314).

As each drug appears on the pump's display screen, the predefined Concentration is displayed along with the assigned drug name. If no predefined Concentration exists for the displayed drug name, dashes are displayed in the Concentration field (i.e., field 4 in FIG. 4). The available choices are determined by which drugs have been configured, and may include a choice of "GENERAL".

Once the desired drug is found, the user selects it by pressing the <CONFIRM> key. In response to the confirm key, the pump selects the drug appearing on the display and prompts the user for the next selection (step 316).

If "GENERAL" is selected (step 318), the pump proceeds to mode selection, and subsequently behaves as if the drug library feature is disabled until it is next powered up (step 320).

In the case of drug entries having identical names and Concentrations but differing in assigned modes, the drug is displayed as one drug entry.

When the <CONFIRM> key is pressed to select a drug entry, if the selected drug entry has more than one assigned mode (step 322), the pump proceeds to mode selection, allowing the user to select between the modes assigned to the drug (step 324). The Concentration field remains displayed during mode selection. If the Drug Default option has been configured (step 326), and the last used drug has been selected, the pump presents the last used mode in response to the first arrow keypress (step 328). Otherwise, the pump displays the first option on the list of available modes (step 330).

The <CONFIRM> key is pressed to select the mode, the pump then reads additional drug library data for the selected drug from the EEPROM (step 334).

If the selected drug has only one assigned mode (in step 322), the pump defaults to that mode and mode selection is skipped (332). The pump then reads additional drug library data for the selected drug from the EEPROM. The assigned mode prompt is displayed in the text field for approximately 2 seconds at the start of syringe manufacturer selection.

The selection of the syringe manufacturer and size are not affected by the drug library feature, except that the predefined Concentration (if any) remains displayed after a drug has been selected. The pump first determines whether there is more than one option configured (step 336). If only one manufacturer has been programmed into the pump, the pump defaults to this option and asks the user to verify that choice (step 338). If there is more than one option, the pump prompts the user to select a manufacturer (step 340). As before, the user presses the arrow keys to enter and move through the list of options. To determine how to respond to the first arrow key press, the pump checks whether the manufacturer default is configured on (step 342). If it is configured on, the pump responds to the first arrow key press by displaying the manufacturer used in the last run (step 344). If the manufacturer default is configured off, the pump responds to the first arrow key press by displaying the first option on the list of options (step 346). When the user has identified the manufacturer of the syringe that is to be used, it is selected by pressing <CONFIRM> (step 348).

After the manufacturer has been selected, the pump checks whether syringe recognition is configured on (step 350). If syringe recognition is configured on, the pump determines the diameter of the syringe barrel and then uses a lookup table for the selected manufacturer to translate that measurement to syringe size. The pump displays the syringe size and prompts the user to verify that size or select a different size (step 352). If syringe recognition is not configured on, the pump prompts the user to select a size (step 354). The user enters the list of options by pressing an arrow key. To determine how to respond to the user's first key press, the pump determines whether syringe default has been configured on (step 356). If syringe default is on, the pump responds to the first arrow key press by displaying the syringe size last run in the pump (step 358). If syringe default is configured off, the pump responds to the first arrow key press by displaying the first (i.e., smallest) option on the list of available syringe sizes (step 360). When the user has identified the syringe size that is to be used, it is selected by pressing <CONFIRM> (step 362).

After the syringe size has been selected, the pump determines whether the selected drug has a predefined concentration (364). If there is a predefined concentration for the selected drug, programming of the concentration field is skipped (step 366). The predefined concentration is assumed to have been selected in the drug selection step and the concentration is displayed in the concentration field of the display. Further, the user will not subsequently be allowed to edit the predefined Concentration field.

If no Concentration is predefined for the selected drug and mode, the pump prompts the user to specify a concentration (step 368).

After the entry in the Concentration field has been established the pump prompts the user to enter a Dose or Rate value (step 370). The predefined default Dose or Rate is displayed.

The user may employ the arrow keys to adjust the displayed value. Or a digit keypress replaces the default value display with the selected digit, allowing direct entry of the desired value. The user may also use the <CLR> key to reset the displayed value to dashes.

Once <CONFIRM> is pressed, if the Dose or Rate is out of the pump's range, the pump displays "PUMP LIMIT" and substitutes the nearest acceptable value.

If the confirmed value is within the pump's range, but out of range for the selected drug, the pump will display "DOSE [or RATE]>nnn" or if the previously programmed value was also out of range for the drug, and in the same direction, it will display "DOSE [or RATE]<nnn" for 2 seconds (where nnn is the drug limit value). The pump then sounds a beep and accepts the confirmed value. If the previous value was not out of range for the drug, or was out of range in the opposition direction, the pump instead sounds a beep, and displays "VERIFY>nnn" or "VERIFY<nnn" (where nnn is the drug limit value). The user may press <CONFIRM> to verify the desired value, or use <CLR>, or digit or arrow keys to change the displayed value. Once the Dose or Rate has been successfully confirmed, the drug name reappears in the text display.

Bolus programming proceeds according to the following rules. If the Bolus function is allowed for the selected drug, and a valid <BOLUS> key is pressed, the pump normally displays the Bolus size. If no Bolus size has been programmed, dashes are displayed in the Bolus size field, and "PRESS EDIT TO SET BOLUS SIZE" will be displayed in the bottom line of the text field as a scrolled prompt. If a Bolus size value has been programmed, it is displayed in the Bolus size field, and "BOLUS READY" is displayed in the text field.

The "BOLUS READY" prompt times out in 10 seconds if no valid key is pressed (the "PRESS EDIT TO SET BOLUS SIZE" prompt will time out in 20 seconds if no valid key is pressed) and the normal Run or Standby state display is restored. However, if the Bolus Size field contains dashes and <START> is pressed, a "DATA MISSING" error response is issued, following which the "PRESS EDIT TO SET BOLUS SIZE" scrolling prompt and its timeout is restarted. If <CONFIRM> or <BOLUS> is pressed following <BOLUS>, the normal Run or Standby display is restored immediately.

If the Bolus Size field does not contain dashes, <START> may be pressed following <BOLUS> to initiate Bolus delivery. If <EDIT> is pressed following <BOLUS>, the pump opens the Bolus size field for editing. "BOLUS SIZE" is then displayed in the text field. If the Bolus size field was displayed as dashes, it is initialized to the predefined default Bolus size for the selected drug.

The <CLR>, arrow or digit keys may be used to edit the Bolus size value. The Bolus size may be set to any value within the pump's limits, as well as to dashes.

If the <EDIT> key is pressed again during Bolus size editing, the pump restores the Bolus size field and text display to their contents when the field was opened, and the Bolus size field is closed.

If an arrow keypress increments or decrements the Bolus size field to a value out of the pump's range, the pump displays "PUMP LIMIT" and substitute the nearest acceptable value.

If the Bolus size field is open for editing, and the value displayed is within both the pump's range and the predefined limits for the selected drug, <CONFIRM> may be pressed to store the Bolus size and close the Bolus size field, or <START> may be pressed to store the Bolus size and initiate Bolus delivery.

If either <CONFIRM> or <START> is pressed and the displayed Bolus size is out of the pump's range, the pump displays "PUMP LIMIT" and substitutes the nearest acceptable value. The Bolus size field remains open, and the key will otherwise be ignored.

If either <CONFIRM> or <START> is pressed and the displayed Bolus size is within the pump's range, but exceeds one of the predefined limits for the selected drug, the pump displays "BOLUS>nnn" or if the previously programmed Bolus size exceeded the same predefined drug limit, it displays "BOLUS<nnn" for 1.5 seconds (where nnn is the predefined drug limit). The pump then sounds a beep, the Bolus size value is stored, and the Bolus size field is closed <CONFIRM>) or the Bolus initiated (<START>).

If the previously programmed Bolus size was not out of range for the drug, or was out of range in the opposite direction, the pump instead sounds a beep, and displays "VERIFY>nnn" or "VERIFY<nnn" (where nnn is the drug limit value). The <CONFIRM> or <START> key will otherwise be ignored. The <CLR>, digit or arrow keys may be used to change the displayed value, or <CONFIRM> or <START> may be pressed to store the Bolus size, and close the Bolus size field (<CONFIRM>) or initiate the Bolus (<START>).

If the Bolus size field is closed by the <EDIT> or <CONFIRM> key and the final displayed value is dashes, the "PRESS EDIT TO SET BOLUS SIZE" scrolling prompt will be displayed. If the value is not dashes, "BOLUS READY" will be displayed. <CONFIRM> and <BOLUS> may be used to reopen the field, as described above. If "BOLUS READY" is displayed, <START> may be pressed to initiate Bolus delivery.

The "BOLUS READY" prompt times out in 10 seconds if no valid key is pressed (and the "PRESS EDIT TO SET BOLUS SIZE" prompt time outs in 20 seconds if no valid key is pressed) and the normal Run or Standby state display is restored.

If the Bolus function is allowed for the selected drug when a valid <BOLUS> key is pressed, but the maximum and minimum Bolus sizes for the selected syringe size lie outside the displayable range, the pump issues an "OUT OF RANGE" error response to the <BOLUS> key.

If the Bolus function is not allowed for the selected drug and an otherwise valid <BOLUS> key is pressed, the pump issues a "NOT ALLOWED" error response to the <BOLUS> key.

If a maximum bolus rate is prespecified for the selected drug, the pump selects the lesser of the maximum bolus rate and the pump maximum rate for the selected syringe, for bolus delivery. If the maximum bolus rate is less than the minimum rate for the selected syringe, the pump issues an "OUT OF RANGE" error response to the <BOLUS> key.

Referring again to FIG. 19c, after the dose (or rate and volume limit) has been appropriately programmed, the user presses the <START> key to begin an infusion. The pump responds differently depending on whether syringe detect is on or off (step 372). If the syringe detect is on, the pump checks whether the syringe is properly mounted before proceeding (step 374). If the syringe is not properly mounted, it alerts the user (step 376). If the syringe is detected as being properly mounted, it begins delivering the drug at the programmed rate and according to the programmed schedule (step 378).

Other Pump Operational Features

The pump has two configuration modes, each of which is selected by entering a special access code immediately after the power-up lamp test. There is a Configuration Set Mode and a Configuration Review Mode. Configuration Set Mode allows the pump configuration to be modified. Configuration Review Mode enables the user to review the current pump configuration but does not allow the user to change the configuration.

Configuration Set Mode:
The configurable options include:

| | |
|---|---|
| Select Drugs? | Individual drugs in the stored drug library can be turned on/off. |
| Select Modes? | Limits the number of modes available to the user. |
| Select Manufacturers? | The pump prompts only for the brands of syringe actually used. |
| Select Defaults? | The pump can be set to default to the drug, mode, manufacturer, and syringe size previously used. |
| Select Misc? | A number of features can be selected including: |

-continued

| | |
|---|---|
| Drug Library | The drug library feature can be toggled on/off. |
| Syringe Recognition | If configured on, the pump automatically determines the size of the syringe. |
| Syringe Detection | If configured on, enables the pump to warn of an improperly mounted syringe. |
| PSI Range | Fine tunes the occlusion alarm by tailoring for the appropriate range of pressures (High, Medium, Low). |
| Rate Range | Limits the maximum delivery rate to High, Medium, or Low range. |
| Auto Lock | Automatically locks the keyboard when the keyboard becomes idle. |
| Volume Limit | Is available in mL/hr mode only and it sounds an alarm when the Volume Limit counts down from the programmed value to zero. |
| Silent Running | Toggles certain alarms on/off. |
| Idle Alarm | Selects the type of idle alarm that will be sounded. |
| Select Ident? | The pump briefly displays a special message when it is turned on. |

The procedure for setting the configuration of the pump requires entering an access code. Thus, this procedure is only available to authorized users who have been given the code. This prevents changes being entered by unauthorized persons. To select the "Configuration Set" Mode, the user enters the special code immediately after the lamp test and the identification has been displayed.

Once in the configuration set mode, the test display area prompts for each option. The user response field (the single-character digit in Field #1) shows the response that is pending. The arrow keys (<▲>, <▼>) enable the user to step through the available choices (including Yes, No, High, Medium, or Low) and pressing the <CONFIRM> key locks in the pending selection.

The first prompt for each option group is a "SELECT| (group name)?" query, where (group name identifies the relevant configurable option. To begin configuring the group, the user selects a pending response prompt of "Y" (yes) and then presses <CONFIRM>. To skip ahead to the next group, the user sets the pending response prompt to "N" (no), and then presses <CONFIRM>.

Once a group has been opened for configuration, every option within that group must be configured. After the final option within a group has been configured, the display read "UPDATING" for a few seconds while the pump's configuration memory is updated, and then it displays the next "SELECT|(group name)?" query.

The following example helps illustrate this procedure. Following mode configuration, the next prompt is "SELECT MFRS?". A flashing "Y" appears in the user response field on the top line of the LCD screen. Pressing <CONFIRM> begins the process of selecting the available syringe manufacturers. The next display is "MONOJECT", identifying a specific manufacturer of syringes, and either a "Y" or "N" in the user response filed of the top line. Pressing <▲> or <▼> toggles the user response between "Y" and "N". Pressing <CONFIRM> enters the selection and causes the next manufacturer to be displayed. After the user has made a selection for all manufacturers, the pump exits "SELECT MFRS?" group and displays the "SELECT DEFAULTS?" prompt, enabling the user to perform the same selection process for the defaults..

Note that the pump program requires that the pump configuration must include at least one mode and manufacturer. The user cannot exit either one of these groups unless there is at least one option selected.

After the last option group has been configured or skipped, the pump terminates the configuration set process by initiating a normal power-up restart.

Configuration Review Mode

The Configuration Review mode allows the pump configuration to be checked without risk of accidental alteration. To review the pump's configuration, the user enters another special access code after the power-up Lamp Test.

The configuration sequence displays the category being reviewed in the lower screen field, followed by a question mark (for example: "VIEW MODES?"). The upper screen field displays a "Y" (for "yes"). Pressing <CONFIRM> begins reviewing the options within this category. The text field displays only the options that are configured. Pressing either <▲> or <▼> changes the "Y" to "N" (for "no"), indicating that review of this category is not wanted. Pressing <CONFIRM> advances the screen to the next category for review.

The Syringe Label Reader

The user can also input relevant information into the pump through touch memory contacts 33, shown in FIG. 1. The user activates this feature through a special key sequence on the control panel. This is done either at the beginning of the process of programming the pump for a particular drug or after the pump has been programmed. Once activated, the contents of the touch memory label transfer into the pump's memory. The transferred information includes, minimally, the drug expiration date, the drug concentration, the manufacturer and the size of the syringe, and the identity of the person who prepared the syringe. An program internal to the pump then performs a number of operations using the transferred information.

Figure 25:
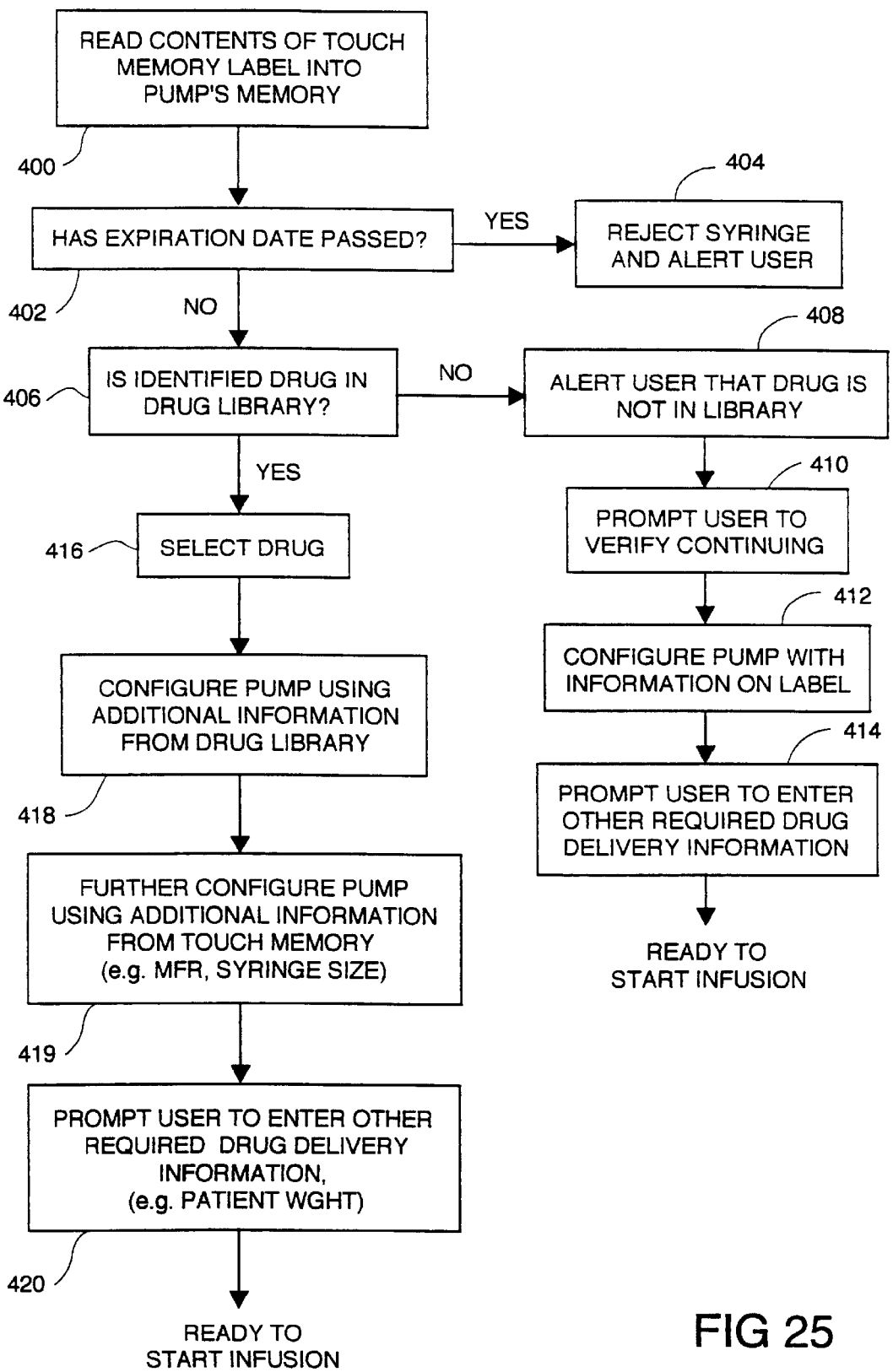
FIG. 25 is a flow chart of the operation of the touch memory function on the drug infusion pump.

If this function is invoked at the beginning of the programming sequence, the program performs the operations shown in FIG. 25. First, the pump receives the contents of the touch memory into its own memory (step 400). Then, the pump checks the syringe's expiration date against the current date (step 402). If the syringe date has expired, the pump rejects the syringe and alerts the user of the expired date (step 404). If the date on the syringe has not expired, the pump program searches its internal drug library for a match with the drug in the syringe (step 406). If no match is found, the pump alerts the user that the drug is not in the library (step 408). The user can continue using the syringe by programming the pump manually without the aid of the drug library. The pump prompts the user to verify whether programming will continue manually (step 410). If the user chooses to continue using that syringe, the program configures the pump using the information available from the label (step 412). Then, the program prompts the user for whatever additional information is required, e.g. dose, rate, bolus size, etc. (step 414). After the pump is fully configured, the pump is ready to run the drug.

If a match is found in the pump's drug library, the pump selects that drug from the drug library (step 416) and configures itself using whatever information has been stored in the library for that drug (step 418). Then, the program further configures the pump using additional information that might be available from the touch memory (e.g. manufacturer, syringe size, etc.). Finally, the pump prompts the user for whatever additional information is required (step 420). Once that information is entered, the pump is ready to run the drug.

As should be readily apparent, by using the touch memory to provide further information useful to configuring the pump (e.g. the inputs previously supplied by the user, see FIGS. 19a–c), the users task in programming the pump can be greatly simplified.

Figure 26:
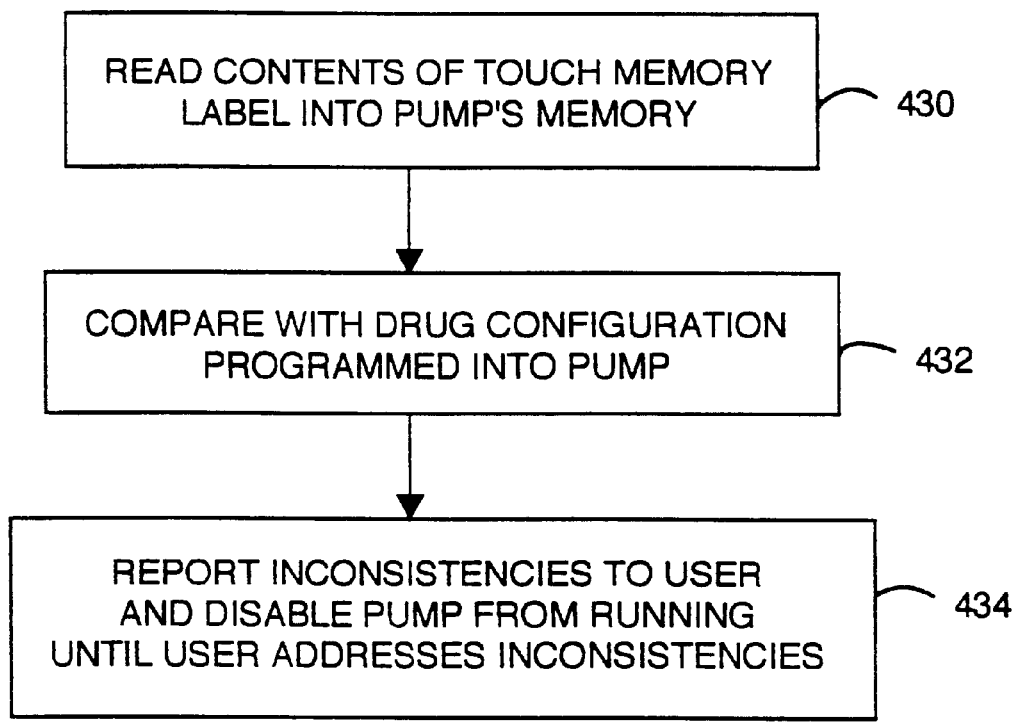
FIG. 26 is another flow chart of the operation of the touch memory function.

If the touch memory feature is used after the pump has been configured for a particular drug, the pump then performs a verification function as illustrated in FIG. 26. After the contents of the touch memory label have been transferred into the pump's memory (step 430), the pump compares the label information with the pump configuration (step 432). If inconsistencies are found, the pump reports those inconsistencies to the user and disables the pump from running the drug until the user either overrides the program or in some other way satisfactorily reconciles the inconsistency (step 434).

The Event Log

As indicated earlier, the pump includes program code that generates an event log 61 in the pump's EEPROM (see FIG. 2). The event log includes a chronological history of program and alarm events with a time stamp for each indicating when the event occurred. Only a preselected number of events is remembered. When the preselected number of recorded events is reached, the record of each new event displaces the oldest event record from memory. The pump uses the event log to record program parameters that were run on the pump, including when infusions were started, when they were stopped, when a bolus was run, when an alarm occurred and the nature of the alarm.

This information can be retrieved from the pump with the aid of the user interface previously described. Referring to FIG. 7, to read the event log, the user selects "LOAD LOG FILE FROM PUMP". In response, the program downloads the contents of the event log into the PC computer from where it can be stored on disk. The event log enables one to reconstruct how a pump has been used in the event that a problem arises that requires such a reconstruction.

Other embodiments are within the following claims.

What is claimed is:

1. A system for creating a customized drug library for an electronically loadable infusion pump, said system comprising:
   a memory for storing a drug library containing a plurality of drug entries, there being associated with each drug entry associated drug delivery information;
   a user interface module enabling a user to select a set of drug entries from among said plurality of drug entries in said drug library, to add the selected drug entries along with the drug delivery information associated therewith to an electronically-stored customized library which presents a plurality of drug selection options to the user of the infusion pump, and to electronically load said electronically-stored customized library into the drug infusion pump.

2. The system of claim 1 wherein each of the associated sets of drug delivery parameters includes information selected from a group of parameters including drug concentration, drug delivery rate, drug dose, and bolus size.

3. The system of claim 2 wherein the said group of parameters includes minimum, default and maximum drug delivery rate.

4. The system of claim 2 wherein the said group of parameters includes minimum, default and maximum dose.

5. The system of claim 2 wherein the said group of parameters includes minimum, default and maximum bolus size.

6. The system of claim 2 wherein the said group of parameters includes maximum bolus rate.

7. The system of claim 1, wherein the user interface module includes an editing module for enabling the user to create a drug configuration with the customized library that does not exist in the drug library.

8. The system of claim 1, wherein the user interface module includes an editing module for enabling the user to edit an existing drug configuration in the customized library.

9. The system of claim 1 further comprising a graphical tool that generates a graph for display on a computer screen, said graph enabling the user to select an appropriate drug concentration for a given body weight.

10. The system of claim 9 wherein said graph is a two-dimensional log—log graph wherein one axis is body weight and the other axis is fluid flow rate.

11. The system of claim 9 wherein one or more curves are plotted on said graph, said one or more curves being for a given drug concentration and different doses.

12. The system of claim 11 wherein the one or more curves are of the form:

$$\text{Body Weight} = \text{Rate} \times \frac{\text{Concentration}}{\text{Dose}} \times K,$$

where K is a positive number.

13. The system of claim 11 further comprising means for moving said one or more curves about on said graph.

14. The system of claim 1 further comprising a list of available mode options, means for identifying one or more modes from said list of available mode options and means for adding said identified modes to said customized library, said modes specifying the units available for expressing the drug delivery information and said identified modes being the modes that will be available in the infusion pump when said customized library is loaded into said infusion pump.

15. The system of claim 14 wherein said available mode options include milliliter/hour, units/hour, micrograms/minute, and micrograms/kilogram/minute.

16. The system of claim 1 wherein said memory stores a list of names of syringe manufacturers, and wherein the user interface also enables the user to select names of syringe manufacturers from said list of names of syringe manufacturers and to add said selected names of syringe manufactures to said customized library, said selected names of syringe manufacturers identifying syringes that the drug infusion pump is configured to work with when said customized library is loaded into said infusion pump.

17. The system of claim 1 wherein said memory stores a list of syringe sizes, and wherein the user interface also enables the user to select one or more syringe sizes from said list of syringe size and to add said selected syringe sizes to said customized library, said selected syringe sizes identifying syringes that the drug infusion pump is configured to work with when said customized library is loaded into said infusion pump.

18. The system of claim 1 wherein the user interface enables the user to specify a set of features within the customized library, each of which is toggled on and off, and wherein the user interface enables the user to toggle each of said features of said set of features on and off.

19. The system of claim 18 wherein said set of features includes a drug library enable flag, wherein the drug library enable flag enables and disables, depending upon the condition of the drug library enable flag, access to the drug entries within the customized library when the customized library is loaded into said drug infusion pump.

20. The system of claim 18 wherein said set of features includes a syringe recognition flag, wherein the syringe recognition flag enables and disables, depending upon the condition of the syringe recognition flag, a syringe recognition capability within said drug infusion pump when the customized library is loaded into said drug infusion pump.

21. The system of claim 18 wherein said set of features includes a syringe detection flag, wherein the syringe detection flag enables and disables, depending upon the condition of the syringe detection flag, a syringe detection capability within said drug infusion pump when the customized library is loaded into said drug infusion pump.

22. The system of claim 18 wherein said set of features includes a volume limit detection flag, wherein the volume limit flag enables and disables, depending upon the condition of the volume limit flag, a function within the pump that enables the user to specify a volume limit for a drug delivery configuration when the customized library is loaded into said drug infusion pump.

23. The system of claim 1 further comprising means for causing said system to read pump configuration information from the drug infusion pump.

24. The system of claim 1 further comprising password protection logic that in a default mode disables the functionality of the user interface that enables a user to select said set of drug entries, wherein said password protection logic enables the functionality of the user interface that enables a user to select said set of drug entries only if a system user supplies a preselected password to said password protection logic.

25. The system of claim 24 wherein there are defined a plurality of access levels, each of said access levels corresponding to a different set of access privileges for said system and wherein said memory also stores a table associating each of a plurality of users with a corresponding one of said plurality of access levels and wherein said password protection logic uses said table to assign access privileges to the system user.

26. The system of claim 25 further comprising an access controller for controlling access to the functionality of the user interface that enables a user to electronically load the customized library into the drug infusion pump, wherein said access controller permits access to the functionality of the user interface that enables a user to electronically load the customized library into the drug infusion pump if a system user satisfies a set of preconditions and denies access to the functionality of the user interface that enables a user to electronically load the customized library into the drug infusion pump if the system user fails to satisfy the set of preconditions.

27. The system of claim 26 wherein said access controller comprises a sign-off table for recording a sign-off and wherein said access controller permits access to the functionality of the user interface that enables a user to electronically load the customized library into the drug infusion pump if a valid approval sign-off exists in said sign-off table and denies access to the functionality of the user interface that enables a user to electronically load the customized library into the drug infusion pump if a valid approval sign-off does not exist in said sign-off table.

28. The system of claim 27 wherein the sign-off table includes a system user name and a system user date and time and an approval name and an approval date and time, wherein said system user date and time records when a last modification of said customized library by said system user occurred and wherein said access controller permits access to the functionality of the user interface that enables a user to electronically load the customized library into the drug infusion pump if said approval date and time is later than said system user date and time and denies access to the functionality of the user interface that enables a user to electronically load the customized library into the drug infusion pump if said approval date and time is later than said system user date and time.

29. A computer-readable medium storing a program that runs on a computer including a storage medium storing a drug library, said drug library containing a plurality of drug entries, there being associated with each drug entry associated drug delivery information for configuring a programmable drug infusion pump, said program for causing the computer to perform the functions of:

enabling a user of said computer to select a set of drug entries from among said plurality of drug entries in said drug library;

enabling the user to add to a customized library the selected set of drug entries along with the drug delivery information associated with each of the drugs in the selected set of drugs; and enabling the user to cause said computer to electronically load the customized library into the drug infusion pump.

30. The computer-readable medium of claim 29 wherein said program is for causing the computer to perform the further function of enabling the user to create a drug configuration within the customized library that does not exist in the drug library.

31. The computer-readable medium of claim 29 wherein said program is for causing the computer to perform the further function of enabling the user to edit an existing drug configuration in the customized library.

32. The computer-readable medium of claim 29 wherein said program is for causing the computer to perform the further function of presenting to the user a graphical tool that generates a graph for display on a computer screen, said graph enabling the user to select an appropriate drug concentration for a given body weight.

* * * * *